US011109992B2

(12) United States Patent
Iwagami

(10) Patent No.: US 11,109,992 B2
(45) Date of Patent: Sep. 7, 2021

(54) PELVIS CORRECTION EQUIPMENT FORMED OF COMBINATION OF PELVIS BELT AND PRESSING CORRECTION EQUIPMENT

(71) Applicant: Akiharu Iwagami, Kumamoto-ken (JP)

(72) Inventor: Akiharu Iwagami, Kumamoto-ken (JP)

(73) Assignee: Akiharu Iwagami, Kumamoto-ken (JP)

(*) Notice: Subject to any disclaimer, the term of this patent is extended or adjusted under 35 U.S.C. 154(b) by 154 days.

(21) Appl. No.: 15/836,009

(22) Filed: Dec. 8, 2017

(65) Prior Publication Data

US 2019/0029864 A1 Jan. 31, 2019

(30) Foreign Application Priority Data

Jul. 25, 2017 (JP) .............................. JP2017-143939

(51) Int. Cl.
*A61F 5/01* (2006.01)
*A61H 7/00* (2006.01)
*A61H 1/00* (2006.01)
*A61F 5/02* (2006.01)
*A61H 1/02* (2006.01)

(52) U.S. Cl.
CPC ............ *A61F 5/0193* (2013.01); *A61F 5/028* (2013.01); *A61H 1/008* (2013.01); *A61H 7/001* (2013.01);
(Continued)

(58) Field of Classification Search
CPC .... A61F 5/0102; A61F 5/0104; A61F 5/0193; A61F 5/028; A61F 5/0292; A61H 1/0292;
(Continued)

(56) References Cited

U.S. PATENT DOCUMENTS 5,913,410 A * 6/1999 Tsuchiya ................. A61F 5/028
128/99.1
6,254,555 B1 * 7/2001 Sevier ..................... A61H 7/001
601/134
(Continued)

FOREIGN PATENT DOCUMENTS

CA 2971972 A1 * 12/2018 ............. A61F 5/028
FR 2872697 A1 * 1/2006 ............. A61F 5/028
(Continued)

OTHER PUBLICATIONS

Yes4All Hexagon Neoprene Coated Dumbbell (Pair)—Multiple Weight Options. Catalogue [Online]. Amazon [Retrieved Sep. 16, 2019] . Retrieved from the Internet: <URL: https://www.amazon.com/Yes4All-Hexagon-Neoprene-Coated-Dumbbell/dp/B075JN9T9Q> (Year: 2019).*
(Continued)

*Primary Examiner* — Rachael E Bredefeld
*Assistant Examiner* — William T Kao
(74) *Attorney, Agent, or Firm* — Lucas & Mercanti, LLP

(57) ABSTRACT

A pelvis correction equipment includes: a pelvis belt for tightening for fastening a lower abdomen of a body, the pelvis belt being used for correcting opening of or strain on a joint portion between a sacral bone and an iliac bone which form a pelvis; a pressing position mark indicated on a surface of the pelvis belt for indicating a plurality of pressing correction portions; and a pressing correction equipment configured to be operated in such a manner that the pressing correction equipment presses the plurality of pressing correction portions along the pressing position mark of the pelvis belt mounted on the lower abdomen by fastening by way of the pelvis belt.

3 Claims, 15 Drawing Sheets

(52) U.S. Cl.
CPC .... *A61H 1/0292* (2013.01); *A61H 2201/0153* (2013.01); *A61H 2201/1253* (2013.01); *A61H 2201/165* (2013.01); *A61H 2201/1628* (2013.01)

(58) Field of Classification Search
CPC .......... A61H 7/00; A61H 7/001; A61H 7/002; A61H 7/003; A61H 7/005; A61H 7/007; A61H 39/00; A61H 39/02; A61H 39/04; A61H 11/00; A61H 2011/005; A61H 1/00; A61H 1/006; A61H 1/008; A61H 2201/0153; A61H 2201/0157; A61H 2201/1253; A61H 2201/1628; A61H 2201/163; A61H 2203/0478
USPC ...................................................... 602/19, 32
See application file for complete search history.

(56) References Cited

U.S. PATENT DOCUMENTS

| | | | | |
|---|---|---|---|---|
| 6,887,211 | B1* | 5/2005 | Sevier | A61H 7/001 |
| | | | | 601/135 |
| 7,556,608 | B2* | 7/2009 | Parizot | A61F 5/028 |
| | | | | 128/96.1 |
| 2009/0198276 | A1* | 8/2009 | Lee | A61F 5/0193 |
| | | | | 606/237 |
| 2019/0029916 | A1* | 1/2019 | Ennis | A61H 1/00 |

FOREIGN PATENT DOCUMENTS

| | | |
|---|---|---|
| JP | 11-56887 A | 3/1999 |
| JP | 2000-308667 A | 11/2000 |
| JP | 2004121785 A | 4/2004 |
| JP | 3115777 U | 11/2005 |
| JP | 2013-005929 A | 1/2013 |

OTHER PUBLICATIONS

JPO, Office Action for the the corresponding Japanese Patent Application No. 2017-143939, dated Jun. 30, 2020, with English translation.

* cited by examiner

SCHEMATIC VIEW OF PELVIS STRUCTURE

PELVIS CORRECTION EQUIPMENT FORMED OF COMBINATION OF PELVIS BELT AND PRESSING CORRECTION EQUIPMENT

CROSS REFERENCE TO RELATED APPLICATION

This application claims the priority of Japanese Patent Application No. 2017-143939 filed on Jul. 25, 2017, which is incorporated herein by reference.

BACKGROUND OF THE INVENTION

1. Field of the Invention

The present invention relates to a pelvis correction equipment formed of a combination of a pelvis belt and a pressing correction equipment used in osteopathy for improving symptoms such as a lumbosacral strain or lumbar hernia.

2. Description of the Related Art

Conventionally, it has been considered that a symptom such as a lumbosacral strain or lumbar hernia is caused by the formation of an unnecessary opening or a strain at a contact portion between a sacral bone which forms a pelvis and has an approximately inverse triangular shape as viewed in a front view and iliac bones which are disposed at positions where the iliac bones are brought into contact with surfaces of both sides the sacral bone, are routed around to back sides of the sacral bone from the sides of the sacral bone and have an approximately semicircular shape as viewed in a plan view, that is, at a sacroiliac joint between the sacral bone and the iliac bones.

Accordingly, it has been medically recognized that a symptom such as a lumbosacral strain or lumbar hernia can be alleviated by correcting this joint portion. That is, the above-mentioned symptoms can be alleviated by correcting a strain or the like on a sacroiliac joint in such a manner that a tension is applied by applying a stimulus to the ligament and the muscle adhering to a joint or such a tension is release by applying a stimulus.

As a technique for correcting such a sacroiliac joint, for example, there has been proposed a pelvis correction belt where a far-infrared-emitting ceramic which stimulates an affected part is disposed at a predetermined position (for example, see JP 11-56887 A) or an pelvis correction equipment which corrects by reducing a load of a weight of a patient on a waist portion by mounting a corset suspended by a support body (for example, see JP 2004-121785 A).

However, neither technique is designed so as to perform pelvis correction by stimulating ligament and muscle adhering to a pelvis. As a result, a technique has been adopted where an operator locates an operation effective position of a pelvis forming tissue based on his experience and acquired technique, applies by pressing a stimulus to a pelvis in a predetermined direction by hand using therapy such as applying a finger pressure thus applying a tension to a ligament and a muscle adhering to a sacroiliac joint or by releasing such a tension whereby abnormality of the pelvis is corrected.

SUMMARY OF INVENTION

In such an operation of correcting a sacroiliac joint based on a technique of an operator, as a matter of course, the difference in technique among operators affects an effectiveness of the operation. Particularly, an operation by hand using therapy such as applying a finger pressure is performed over a wide area of a pelvis for a long time and hence, there may be a case where a finger pressure tool having a predetermined shape is used for reducing a load of such a therapeutic operation.

However, there may be a case where when a therapeutic operation is inadvertently applied to a portion of a body displaced from a correction effective position using a finger pressure tool, an affected part is worsened to the contrary resulting in that a correction effect not being expected.

To overcome the above-mentioned drawbacks of the related art, the first embodiment of the present invention provides a pelvis correction equipment formed of a combination of a pelvis belt and a pressing correction equipment, the pelvis correction equipment includes:

the pelvis belt for tightening for fastening a lower abdomen of a body, the pelvis belt being used for correcting opening of or strain on a joint portion between a sacral bone and an iliac bone which form a pelvis;

a pressing position mark indicated on a surface of the pelvis belt for indicating a plurality of pressing correction portions; and the pressing correction equipment configured to be operated in such a manner that the pressing correction equipment presses the plurality of pressing correction portions along the pressing position mark of the pelvis belt mounted on the lower abdomen by fastening by way of the pelvis belt, and also configured to be therapeutically operated vertically, laterally or in a semicircular shape when necessary, wherein the pressing correction equipment has: a proximal portion which forms a pressing grip portion; and a distal end portion which forms an elongated pressing functional part having a cross section where an approximately tip end is sharpened.

According to the second embodiment, the pressing correction equipment is formed of an approximately L-shaped cross-sectional portion made of a hard material having a large wall thickness, a raised side portion of the approximately L-shaped cross-sectional portion forms the pressing functional part where a distal edge portion is formed in an approximately straight line shape or a gentle approximately curved shape as viewed in a front view and is formed such that a wall thickness is gradually decreased toward a distal end as viewed in a side view, and a lateral side portion of the approximately L-shaped cross-sectional portion is a largest wall thickness portion and forms the pressing grip portion during a pressing correction operation.

According to the third embodiment, the pelvis belt is formed of an extendable and shrinkable elastic belt, and an overlapping fixing means of a belt body is mounted on an end portion of the pelvis belt.

According to the fourth embodiment, the pressing position mark indicated on the surface of the pelvis belt is a longitudinal line which traces the pressing correction position on the pelvis.

According to the fifth embodiment, the pressing position mark indicated on the surface of the pelvis belt is a schematic view of a pelvis structure of a human body which allows the visual recognition of the pressing correction position on the pelvis.

According to the sixth embodiment, a surface of a portion of the pressing position mark indicated on the surface of the pelvis belt has a slip preventing function so as to make slipping of the pressing functional part of the pressing correction equipment difficult.

According to the first embodiment of the invention, it is possible to acquire an advantageous effect where the pressing position which is most effective during pressing therapy for strain or displacement of a pelvis joint can be visually recognized by the pelvis belt. Further, predetermined pressing therapy can be performed by placing the pressing functional part of the pressing correction equipment on the visually recognized pressing position. Accordingly, it is possible to acquire an advantageous effect where the proper correction of abnormality of a pelvis can be performed with least labor.

That is, a pelvis tissue group such as a pelvis structure or a muscle and ligament adhering to the pelvis structure is brought into a fixed state by fastening the belt to a contact position of a sacral bone and an iliac bone of a sacroiliac joint which is movable and unstable during pressing therapy. Accordingly, an equipment pressing force generated by the pressing correction equipment is effectively transmitted to the pelvis structure and hence, there is no possibility that unduly large stress is applied to a pelvis whereby the pelvis tissue group which embraces the pelvis is activated. Accordingly, the pelvis tissue group corrects the iliac bone and the sacral bone displaced from each other and introduces both the iliac bone and the sacral bone to respective proper positions thus realizing the correction of the pelvis.

According to the second embodiment of the invention, by placing the pressing position mark to the pressing correction equipment as described above, a pressing force can be properly transmitted to the pressing position mark while securely gripping the grip portion during pressing therapy. Further, the pressing functional part is formed in an elongated shape and having a sharpened distal end and hence, the pressing functional part can functionally cure a joint of this abnormality by stimulating various muscles and ligaments relating to a sacroiliac joint of a pelvis. Accordingly, a uniform therapy can be applied to a patient regardless of a technique of an operator.

That is, with the use of the pressing correction equipment which is brought into contact with the pressing position mark indicated on the surface of the pelvis belt, a proper pressing therapeutic stress can be generated so that correction pressing can be performed. Accordingly, the pelvis correction equipment can acquire an effect of correcting a strain on a sacroiliac joint or the like rapidly, accurately and with certainty.

Further, unlike a simple plate-like pressing finger pressure plate, the pressing correction equipment has the approximately L-shaped pressing grip portion, and the distal end of the pressing portion forms a straight-like or gently-curved-shaped and gradually-decreased-wall-thickness pressing functional part. Accordingly, it is possible to accurately place the pressing functional part to the pressing position mark and eventually, a stimulus position of a human body, muscles or the like relating to a sacroiliac joint, and a pressing stress of an operator can be applied to a correction effective position of the sacroiliac joint to the maximum by way of the pressing position mark cooperatively with a proper grip function.

According to the third embodiment of the invention, the pelvis can be tightened by wrapping the pelvis belt around the pelvis. Accordingly, a correction function of the pressing correction equipment can be further enhanced thus further enhancing an effect of curing the sacroiliac joint of the pelvis of this abnormality.

According to the fourth embodiment of the invention, the position mark which corrects abnormality of a sacroiliac joint is indicated by a longitudinal line. Accordingly, it is possible to correctly place the longitudinal pressing functional part of the pressing correction equipment and hence, a therapeutic effect can be further enhanced.

According to the fifth embodiment of the invention, the positions of the sacroiliac joint of the pelvis and the position of the pressing correction are visually recognized as drawings of the actual human body pelvis structure. Accordingly, a therapeutic position can be confirmed while recognizing the actual pelvis structural tissue of the human body and hence, it is possible to acquire a therapeutic effect substantially equal to a therapeutic effect acquired by visual therapy.

According to the sixth embodiment of the invention, the surface of the portion of the pressing position mark indicated on the surface of the pelvis belt maintains a slip preventing function so as to make slipping of the pressing functional part of the pressing correction equipment difficult. Accordingly, the pressing functional part of the pressing correction equipment can properly transmit a pressing stress onto an affected part without causing slipping of the pressing functional part of the pressing correction equipment during the operation and hence, the sacroiliac joint of the pelvis can be cured of this abnormality thus enhancing a correction function.

DESCRIPTION OF PREFERRED EMBODIMENTS

Hereinafter, an embodiment of the present invention is described in detail with reference to drawings. In the description made hereinafter, a pelvis belt which forms a pelvis correction equipment is described first. Next, a pressing correction equipment is described. Lastly, an in-use example of the pelvis correction equipment according to the present invention is described.

[1. Pelvis Belt]

Figure 1A:
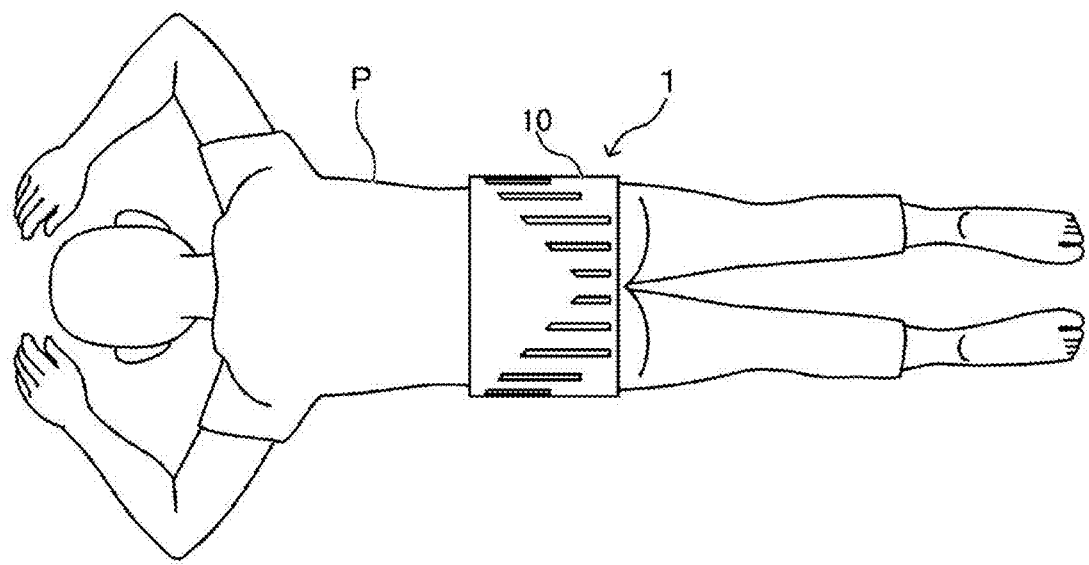
FIG. 1A and FIG. 1B are explanatory views showing the configuration of a pelvis belt of a pelvis correction equipment according to the present invention.
Figure 1B:
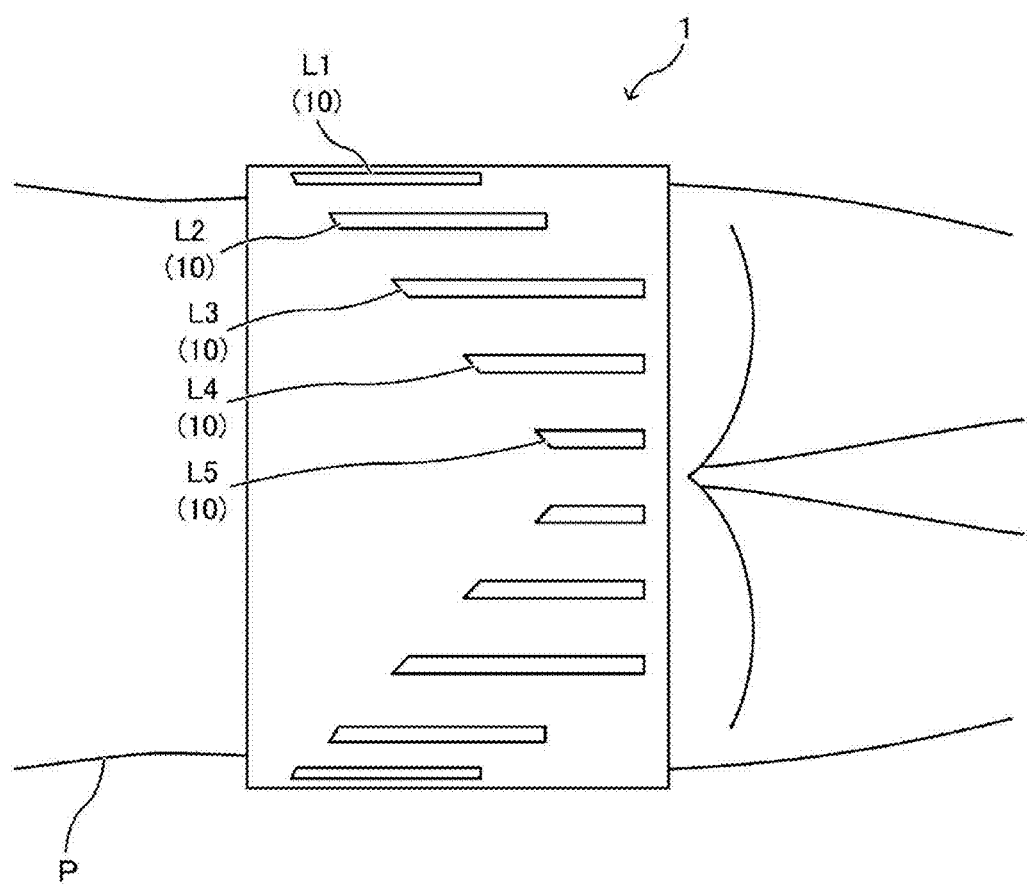
Figure 2A:
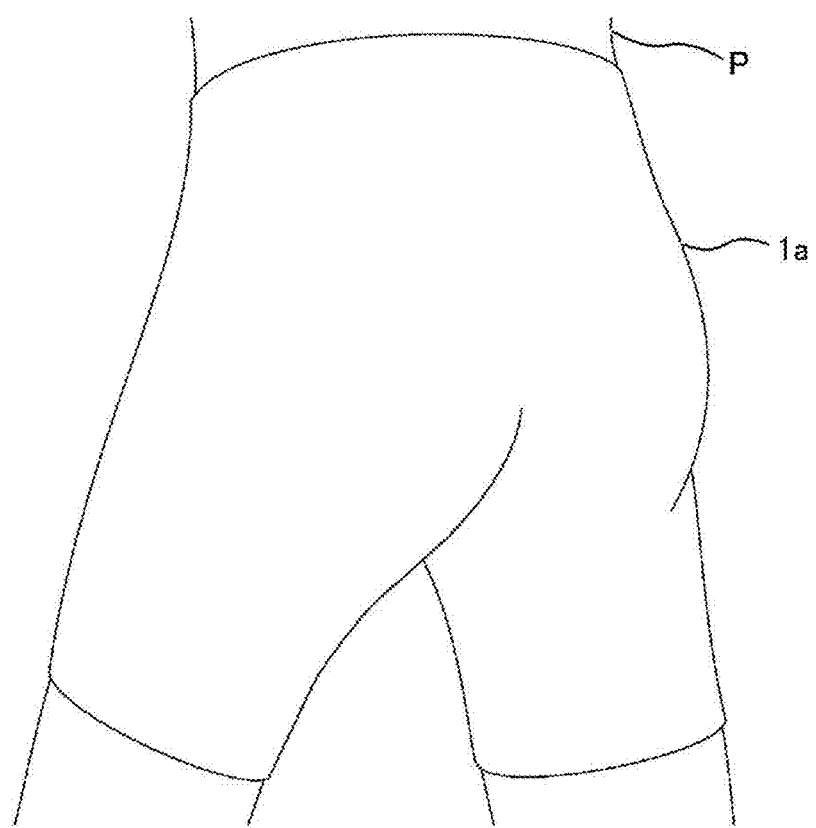
FIG. 2A and FIG. 2B are explanatory views showing the configuration of a modification of the pelvis belt of the pelvis correction equipment according to the present invention.
Figure 2B:
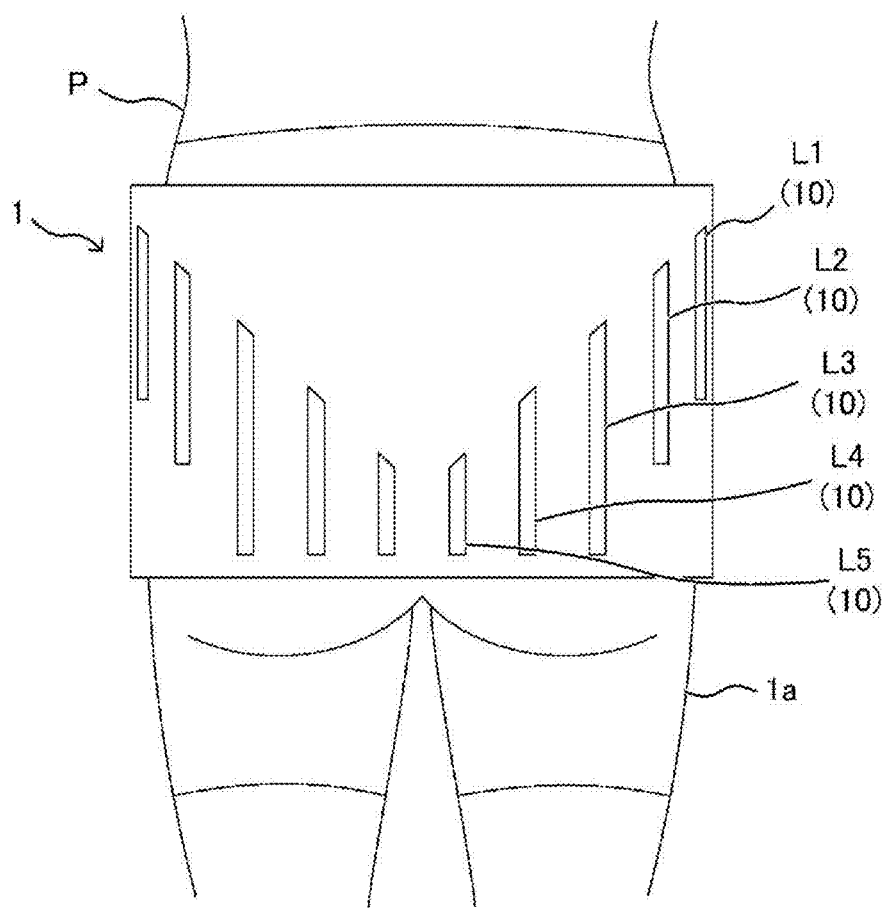
Figure 3:
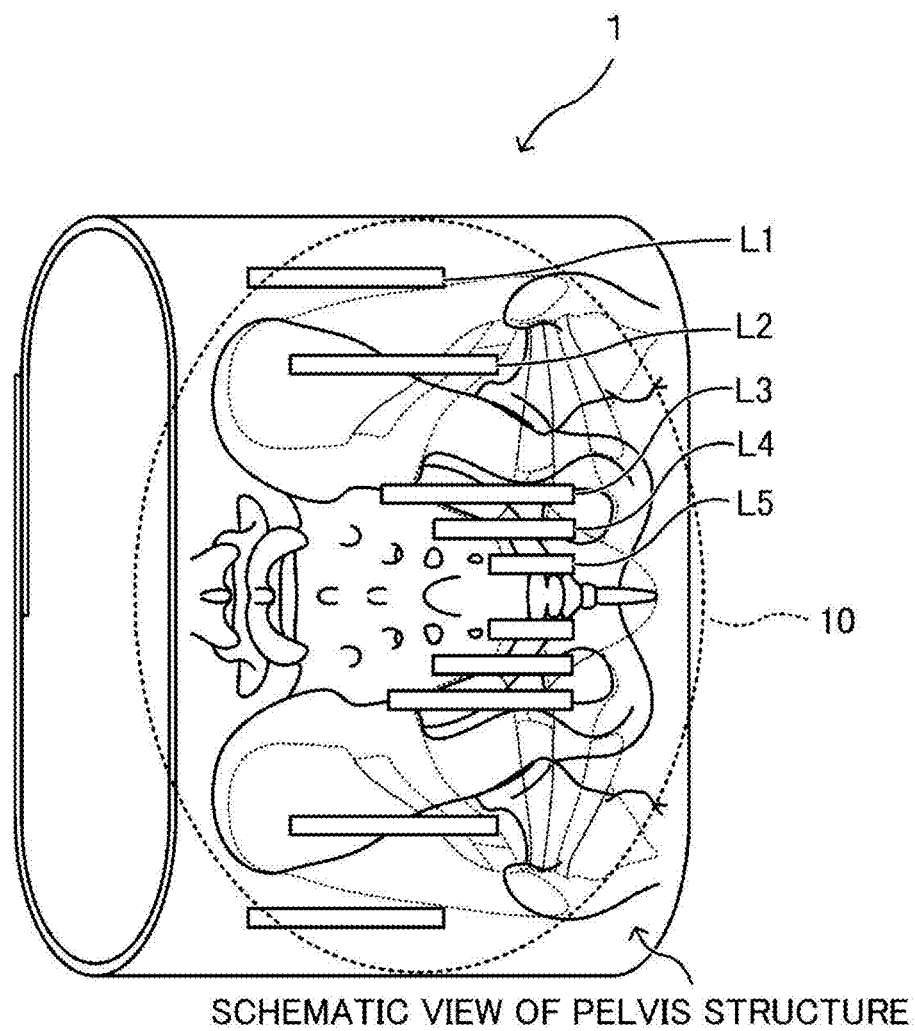
FIG. 3 is an explanatory view showing the configuration of another modification of the pelvis belt of the pelvis correction equipment according to the present invention.
Figure 9:
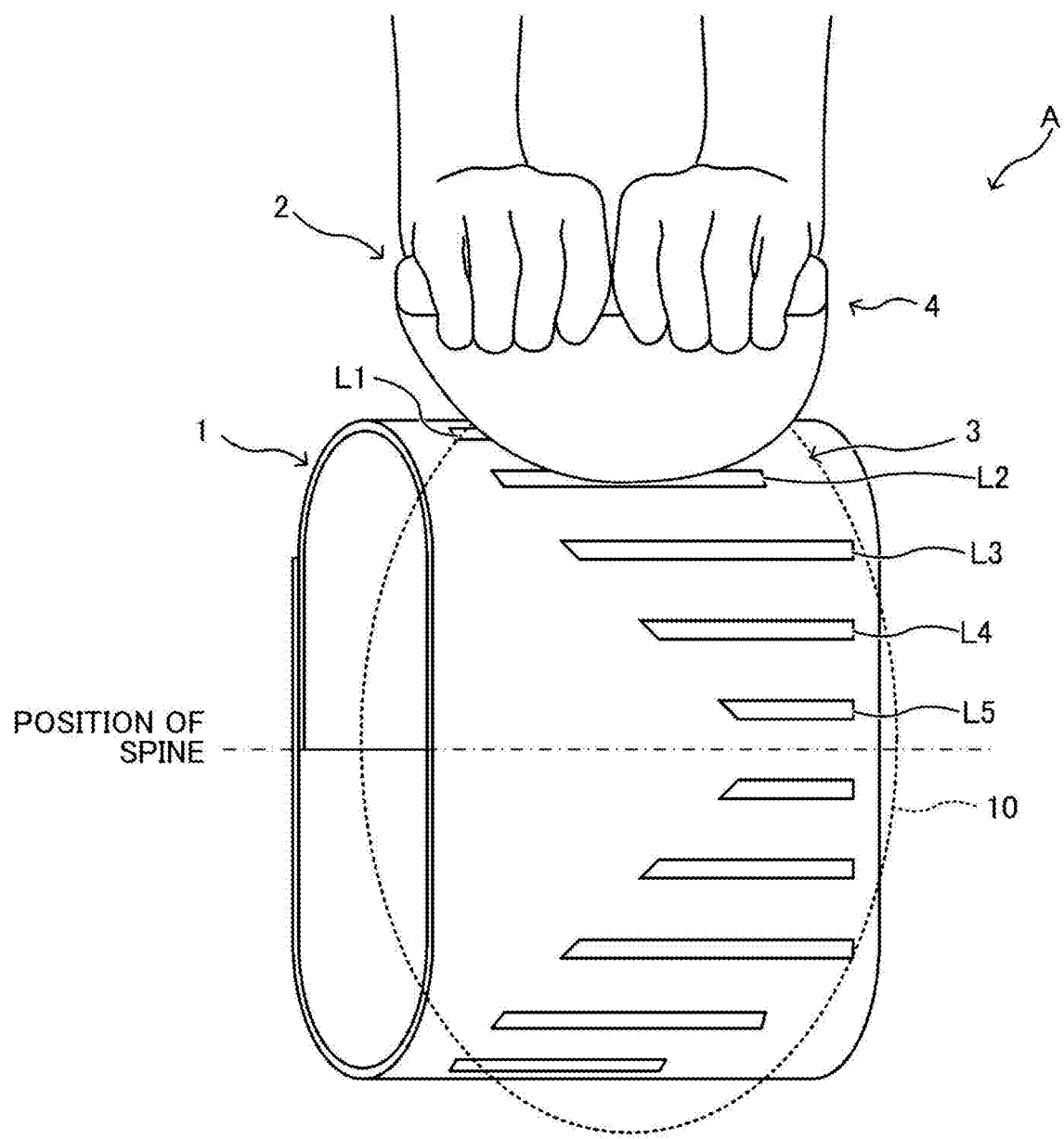
FIG. 9 is a plan view showing an in-use state of the pelvis correction equipment according to the present invention.
Figure 10:
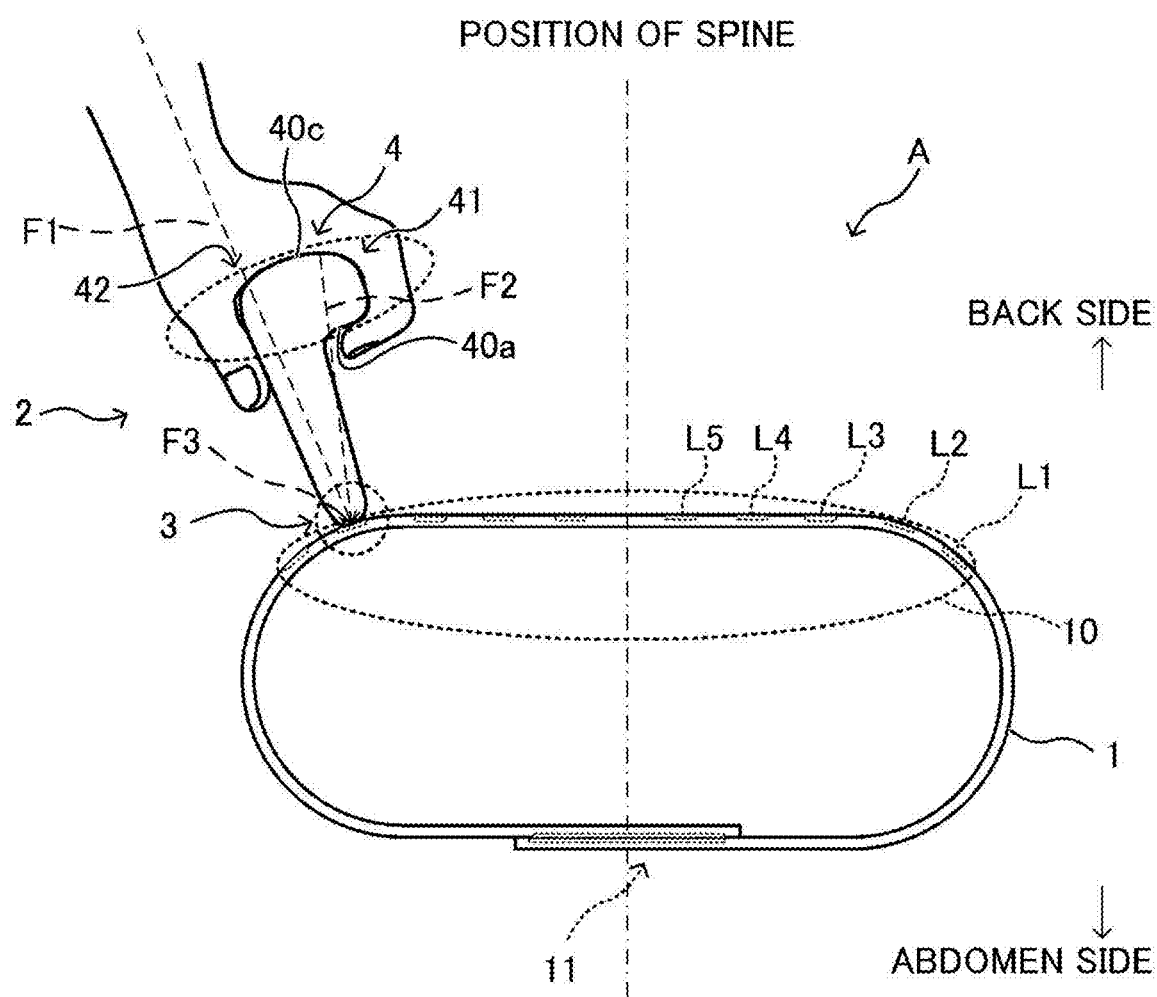
FIG. 10 is a side view showing the in-use state of the pelvis correction equipment according to the present invention.
Figure 11:
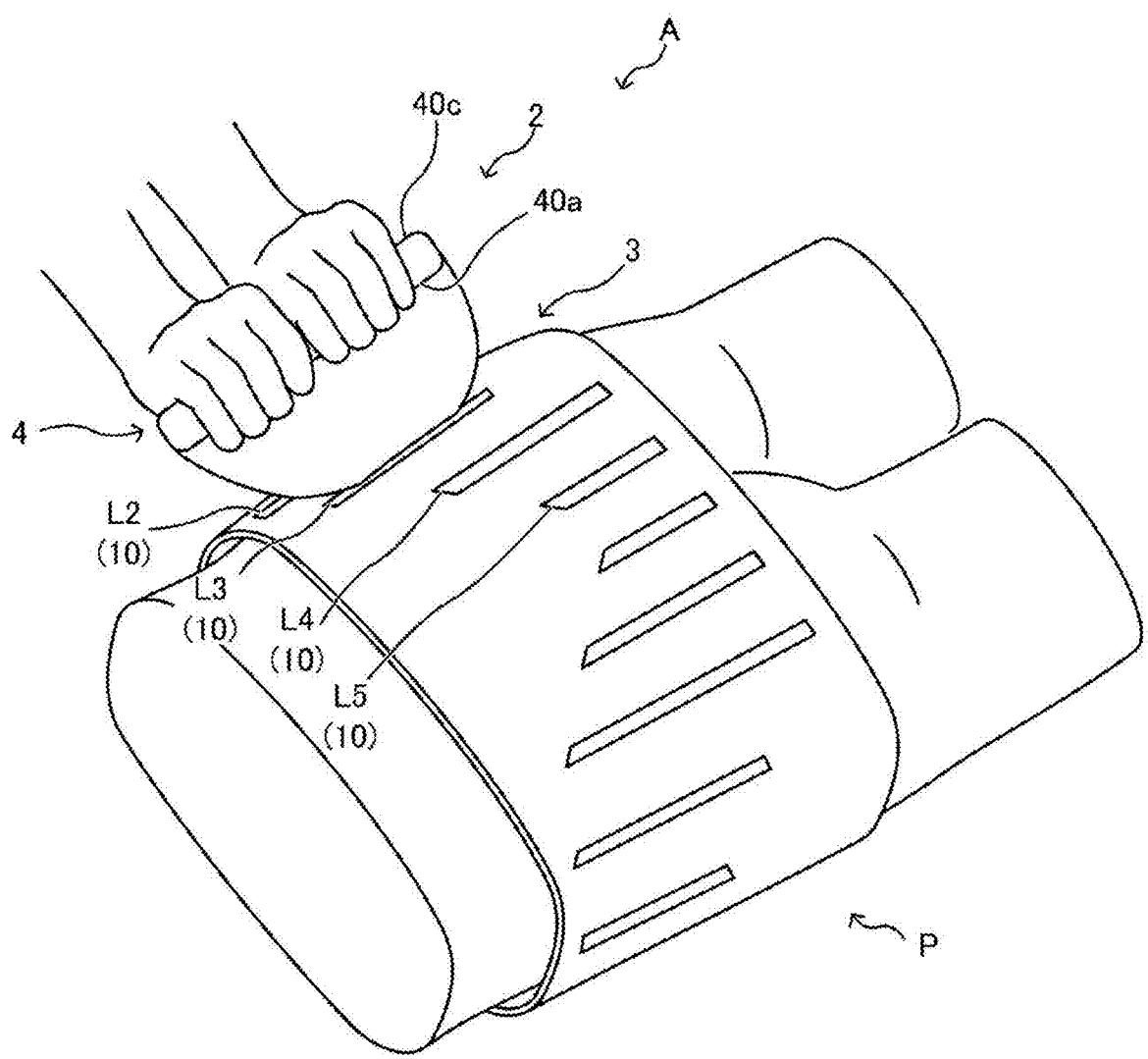
FIG. 11 is an external appearance perspective view showing the in-use state of the pelvis correction equipment according to the present invention.
Figure 12:
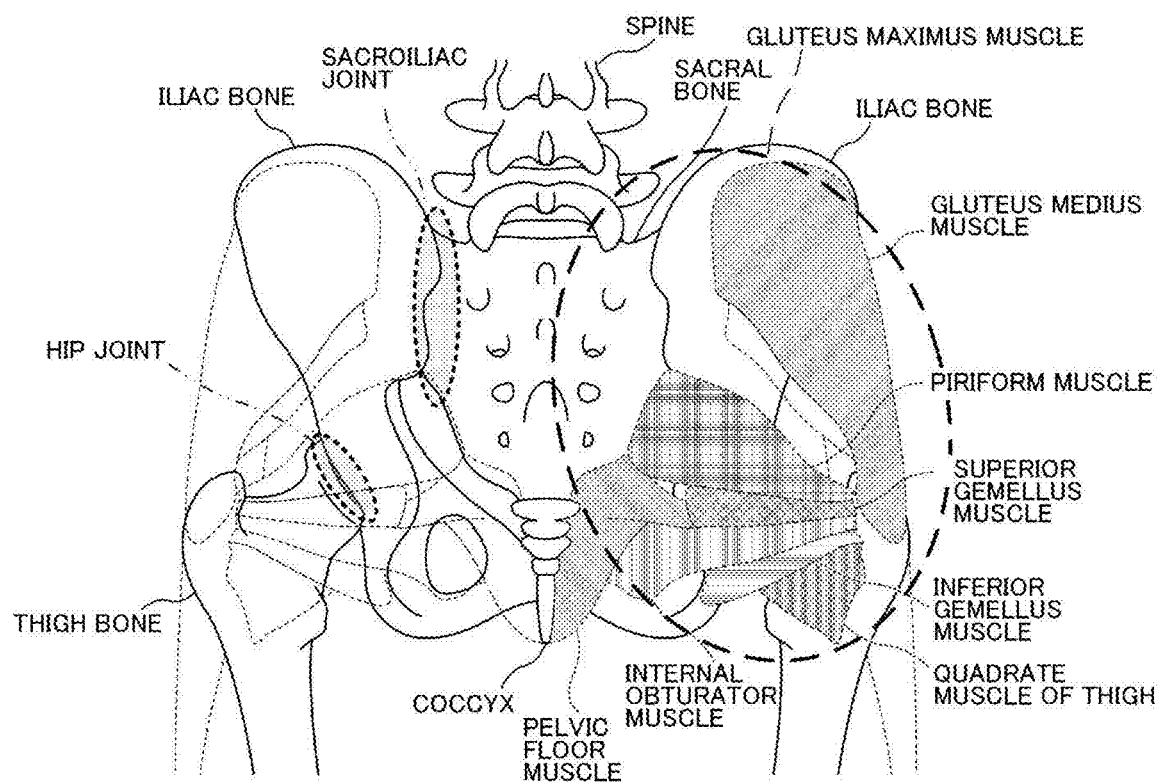
FIG. 12 is a schematic front view showing a pelvis to which an operation is applied by the pelvis correction equipment according to the present invention.
Figure 13:
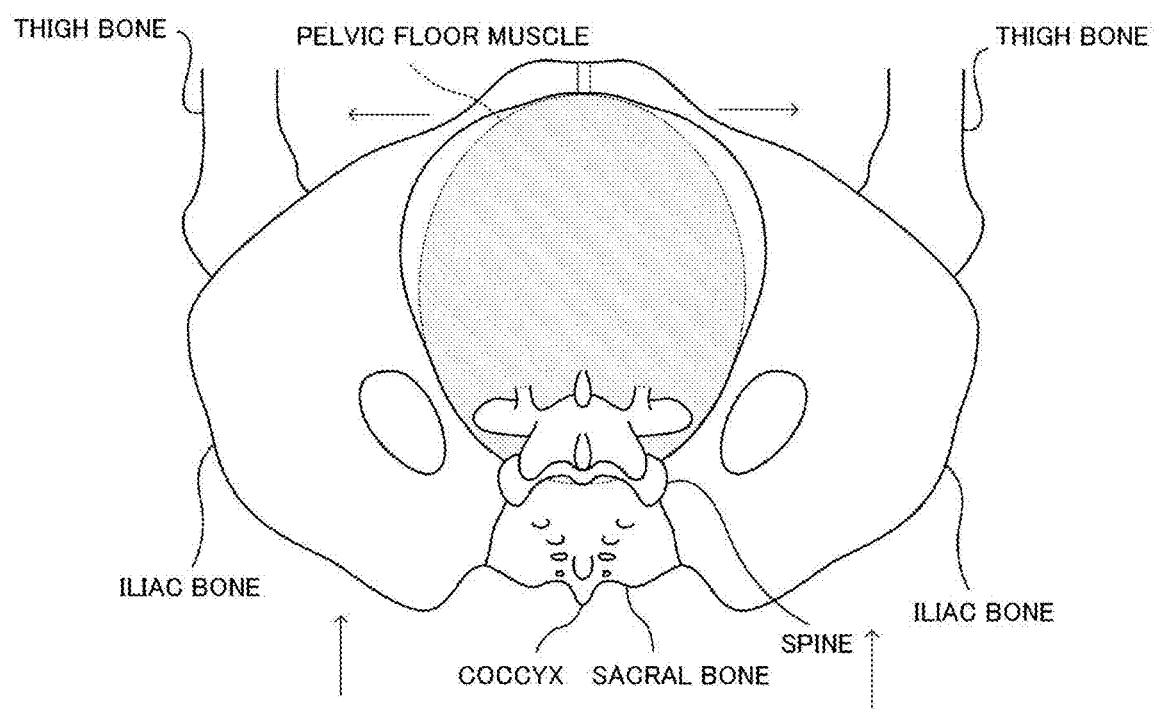
FIG. 13 is a schematic plan view showing the pelvis to which an operation is applied by a pelvis correction equipment according to the present invention.
Figure 14:
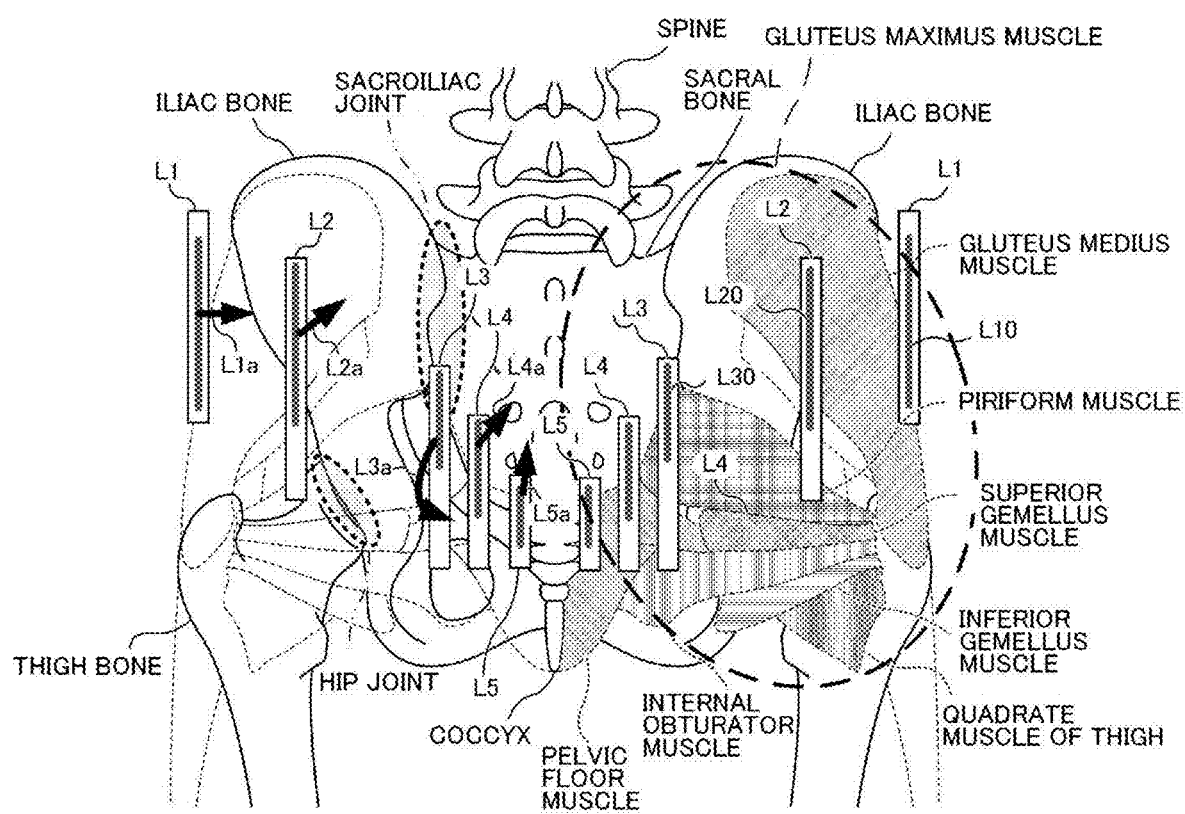
FIG. 14 is a front view showing a positional relationship between a pressing position mark of the pelvis correction equipment according to the present invention and a pelvis to which an operation is applied.

FIG. 1A and FIG. 1B are explanatory views showing the configuration of a pelvis belt, and FIG. 2A to FIG. 3 are explanatory views showing the configurations of modifications of the pelvis belt. FIG. 9 is a plan view showing an in-use state of a pelvis correction equipment, FIG. 10 is a side view showing the in-use state of the pelvis correction equipment, FIG. 11 is an external appearance perspective view showing the in-use state of the pelvis correction equipment, FIG. 12 is a schematic front view showing a pelvis, FIG. 13 is a schematic plan view showing the pelvis, and FIG. 14 is a front view showing a positional relationship between a pressing position mark of the pelvis belt and a pelvis.

As shown in FIG. 1A and FIG. 1B, the pelvis belt 1 is formed of a strip body having a fixed width and a length which allows the pelvis belt 1 to be wrapped around a pelvis portion in a tightened state.

To be more specific, as shown in FIG. 1A, the pelvis belt 1 is formed of an elastic material which can fasten a pelvis when being wrapped around so as to cover a lower abdomen of a human body P, that is, a waist portion and buttocks of the human body P by making the pelvis belt 1 function such that the pelvis belt 1 fasten the pelvis from a surface of the waist portion due to an elastic function of such an elastic material, a shape of the waist portion of the human body P can be made externally apparent in a state where the pelvis belt 1 is wrapped around the human body P.

A raw material of the pelvis belt 1 is not particularly limited provided that the raw material is a fabric made of a raw material having stretchability, that is, elasticity and flexibility. For example, the raw material may be polyurethane, polyester, a synthetic fabric such as a foamed rubber sheet or a natural rubber sheet, a natural fabric in which elastic rubber is interwoven. A extensible and shrinkable natural rubber sheet is adopted as a raw material of the pelvis belt 1 in this embodiment.

A thickness of the pelvis belt 1 can be suitably changed corresponding to elasticity or flexibility of a raw material. That is, the thickness of the pelvis belt 1 is set to a thickness which allows the pelvis belt 1 to have a function of buffering an excessive pressing force caused by the pressing correction equipment 2 described later and allows effective applying of a pressing force for an operation on an affected part. The thickness of the pelvis belt 1 according to this embodiment is set to approximately 1.0 mm to 2.0 mm.

A raw material or working which performs a slip preventing function is applied to a surface of the pelvis belt 1, particularly to a surface of a portion of the pelvis belt 1 at the pressing position mark for making slipping of the pressing functional part of the pressing correction equipment difficult.

A slip preventing function is imparted to a surface of the pelvis belt 1, for example, in case of a fabric belt, by weaving the pelvis belt 1 using bold threads such that the surface has fixed unevenness, and by applying a slip preventing function to the surface by adhering very fine particles to the surface as surface roughening processing.

What is important here is that the pressing operation is applied to the pelvis belt 1 from the surface of the pelvis belt 1 using the pressing correction equipment 2 for pelvis correction. Accordingly, it is necessary to prevent the occurrence of slipping on the surface of the pelvis belt 1 by the pressing correction equipment 2. For this purpose, it is possible to apply a slipping prevention function other than the above-mentioned method.

For example, when a foamed rubber sheet is adopted as a raw material of the pelvis belt 1, in pressing the pelvis belt 1 by the pressing correction equipment 2, it is possible to make the surface of the pelvis belt 1 to acquire a slipping prevention function by bringing a surface of a distal end portion of the pressing correction equipment 2 into contact with a numerous number of foamed apertures uniformly exposed on the surface of the pelvis belt 1 and, at the same time, it is possible to make a large amount of foam in the pelvis belt 1 function as a buffer material for buffering an excessively large pressing force.

A shape of the pelvis belt 1 is not particularly limited provided that the pelvis belt 1 be a strip body having a length and a width which allows wrapping of the pelvis belt 1 having a fixed width around a pelvis portion in a tightened state. For example, a stream-line shape which conforms to curved surfaces of a pelvis portion of a patient, that is, curved surfaces of buttocks or a abdomen raised in front of and behind a waist portion of a patient may be formed into an approximately recessed shape in a width direction. In this embodiment, a long side length and a short side length of the pelvis belt 1 are set to approximately 110 to 130 cm and approximately 25 to 35 mm such that the pelvis belt 1 conforms to a waist size of a normal adult male.

To simply describe a width of the pelvis belt 1, the width is set such that an upper edge portion of the pelvis belt 1 reaches a navel portion of a human body and a lower edge portion of the pelvis belt 1 covers a coccyx.

When the pelvis belt 1 having such a configuration is wrapped around a waist portion of a patient, the pelvis belt 1 has an effect of preventing a load caused by an unnecessary tightening stress applied to the buttocks and the abdomen from being applied to a patient. Further, the pelvis belt 1 has a fixed width and shape and hence, when the patient wears the pelvis belt 1, he can properly wear the pelvis belt 1 securely at a pelvis position. Accordingly, a pressing correction operation which follows such a wearing operation can be performed with certainty.

As shown in FIG. 10, the pelvis belt 1 includes a belt overlapping fixing unit 11 such as a hook and loop fastener or engaging hooks at end portions thereof for fixing the pelvis belt 1 after wrapping the pelvis belt 1 around the pelvis portion in a tightened state.

With respect to the shape of the pelvis belt 1 having the above-mentioned configuration, as shown in FIG. 2A, as another modification, it may be possible to use a short-pants-like fitting jig 1a which fits onto a body.

That is, as shown in FIG. 2B, a user wears the short-pants-like fitting jig 1a such that the fitting jig 1a covers an area from a thigh portion to a waist and, at the same time, the pelvis belt 1 according to the present invention tightens a body ranging from a coccyx to a pelvis in an overlapping manner.

A plurality of pressing portion marks 10 are indicated on the surface of the pelvis belt 1 at positions where pressing correction is applied.

That is, the pressing portions marks 10 indicated on the surface of the pelvis belt 1, as shown in FIG. 1B and FIG. 11, are indicated such that vertical bold lines having predetermined lengths are disposed at a therapy pressing positions about a sacroiliac joint of a pelvis structure such that the vertical lines are laterally arranged parallel to each other at a fixed interval.

The indication positions of the pressing position marks 10 are determined such that the indication positions are at eccentric positions by taking into account an overlapping position where the end portions of the strip-like pelvis belt 1 overlap with each other when the pelvis belt 1 is wrapped around a waist portion of a patient and are fixed to each other by the overlapping fixing means 11 in a longitudinal direction of the pelvis belt 1.

The vertical lines which form the pressing position marks 10 are symmetrically indicated at five places on left and right half portions (ten places in total in the lateral direction) as the most representative sacroiliac joint operation positions. However, the positions of the vertical lines are not necessarily limited to such positions, and the number of indication positions can be suitably decreased or selected.

That is, the sacroiliac joint operation positions can be changed and indicated in conformity with sex, age, a physique of a patient. In this embodiment, among the pressing position marks 10 in the respective left and right halves, the pressing position marks 10 in the left or right half are described.

In this specification, the terms used relating to the pelvis structure correction method have the following definitions (see FIG. 12 and FIG. 13).

(Terms Regarding the Bones)
sacral bone: a bone forming a pelvis having an approximately inverse triangular shape as viewed in a front view
iliac bones: a pair of bones forming a pelvis which are disposed at positions where the iliac bones are brought into contact with surfaces of both sides the sacral bone, are routed around to back sides of the sacral bone from the sides of the sacral bone and have an approximately semicircular shape as viewed in a plan view
coccyx: a bone of a sharp portion positioned at a lowermost portion of a sacral bone and usually referred to as a tailbone
thigh bone: an elongated and thick bone which forms a center axis of a thigh
spine: bones connected to a sacral bone at a lower end thereof forming a body axis and, particularly, a lower portion of the spine being referred to as lumbar vertebrae (Terms Regarding Joints)
sacroiliac joint: a contact portion between a sacral bone and a iliac bone
hip joint: a contact portion between an upper end of a thigh bone and a lower outer side of an iliac bone (Terms Regarding Muscles)
gluteus maximus muscle: muscle extending to an outer side portion of thigh muscle as well as a rear front portion of a thigh bone from an outer side of a sacral bone and a coccyx so that the gluteus maximum muscle covers gluteus medius muscle, piriform muscle, superior and inferior gemellus muscles, and internal obturator muscle and positioned at a most surface side
gluteus medius muscle: muscle extending from an outside of an upper portion of the iliac bone to a spherical protrusion of an outside of an upper portion of a thigh bone
piriform muscle: muscle extending to a spherical protrusion of a thigh bone at an upper outer side from an inner side of a lowermost portion of a sacral bone
superior gemellus muscle: muscle extending to a spherical protrusion of an upper portion of a thigh bone from a spinous protrusion of an outer side of a lower portion of an iliac bone
internal obturator muscle: muscle extending to a base of a spherical protrusion of an upper portion of a thigh bone from an inner side surface of a lower portion of an iliac bone
inferior gemellus muscle: muscle extending to a base of a spherical protrusion of an upper portion of a thigh bone from an outer side of a lowermost portion of an iliac bone
pelvic floor muscle: film-like muscle extending from a bottom portion of a sacral bone toward a bottom portion of an iliac bone so as to cover a bottom portion of a pelvis structure
quadrate muscle of thigh: muscle extending to a spherical protrusion of an outer side of an upper portion of a thigh bone from an outer side of a lower portion of an iliac bone Hereinafter, in this embodiment, the description is made with respect to a mode of a pressing therapy using the pressing correction equipment 2 where the lines at five places are referred to as the first, second, third, fourth and fifth lines, and the positions of the lines on the surface of the pelvis belt 1 and the respective lines are used as marks in accordance with pelvis structure schematic views shown in FIG. 12 and FIG. 13 (the directions described in the description of this specification being left and right directions, upward and downward directions, inclined directions and an arcuate in a state where a human body stands).

As shown in FIG. 14, the first lines L1 are arranged at positions which correspond to approximately upper half portions of outermost side surfaces of the left and right half iliac bones which form the sacroiliac joint, and which also correspond to positions above outer portions of gluteus maximus muscle.

The second lines L2 are arranged at positions which correspond to positions where the second line L2 strides over respective portions consisting of an approximately center portion of a gluteus medius muscle and an outer portion of a piriform muscle at approximately upper half portions of center portions of the left and right half iliac bones which form the sacroiliac joint.

The third lines L3 are arranged at positions which correspond to positions where the third line L3 strides over respective portions consisting of a body axis side portion of a piriform muscle disposed closed to the sacroiliac joint, an outer portion of a pelvic floor muscle and a body axis side portion of an internal obturator muscle.

The fourth lines L4 are arranged at positions which correspond to positions above approximately left and right half portions of the pelvic floor muscle at left and right sides of lower halves of lower portions of the sacral bone which form the sacroiliac joint.

The fifth lines L5 are arranged at positions which correspond to areas above approximately center portions of the pelvic floor muscles at side edge portions extending to a coccyx from sacral bone peaks positioned at lowermost portions of the sacral bones which form the sacroiliac joint.

In this embodiment, the respective vertical lines which are the pressing position marks 10 indicated on the pelvis belt 1 are formed on the surface of the pelvis belt 1 as grooves having a recessed shape in cross section, and the pressing functional part 3 of the pressing correction equipment 2 having a gradually thinned wall thickness is tightly fitted in a bottom portion of the recessed groove. Accordingly, the pressing functional part 3 is fixedly positioned at a correct position so that the pressing functional part 3 is not displaced during pressing therapy and, at the same time, a pressing stress of the pressing correction equipment 2 is smoothly transmitted to curative position on the pelvis.

The respective vertical lines of the pressing position marks 10 indicated on the pelvis belt 1 may be formed of a raw material having larger flexibility than regions of the pelvis belt other than the respective vertical lines.

Further, as shown in FIG. 3A and FIG. 3B, the pressing position marks 10 indicated on the surface of the pelvis belt 1 may be indicated by using a schematic view of a pelvis structure of a human body shown in FIG. 12 which enables a user to visually recognize pressing correction positions of the pelvis.

To be more specific, the schematic view of a pelvis structure of a human body is indicated on the surface of the pelvis belt 1 corresponding to the pelvis correction. When the pelvis belt 1 is wrapped around a waist portion of a patient, an actual pelvis structure of a patient and a schematic view of a pelvis structure indicated on the surface of the belt agree with each other. Accordingly, actual configuration of the pelvis structure of the patient can be visually recognized through the schematic view of the pelvis structure indicated on the surface of the belt.

In indicating the pressing position marks 10 such as the vertical lines and the schematic view of a pelvis structure on the surface of the pelvis belt 1, the indication is made on the surface of the belt by printing.

In place of the belt, a user may wear leggings (short pant) 1a indicated in FIG. 2A in place of the belt, and a schematic view of the pelvis structure may be depicted, by a method such as printing, on a pelvis structure corresponding portion of the leggings 1a made of a raw material formed of cloth fibers when the user wears the leggings 1a, for example, on a back surface portion of the leggings 1a which corresponds to a waist of the user.

A patient wears the leggings 1a in place of wrapping his waist with the above-mentioned pelvis belt 1, and applies a pressing therapy on predetermined positions based on the pelvis structure view depicted on the leggings 1a in place of the structure view on the pelvis belt 1.

Figure 5:
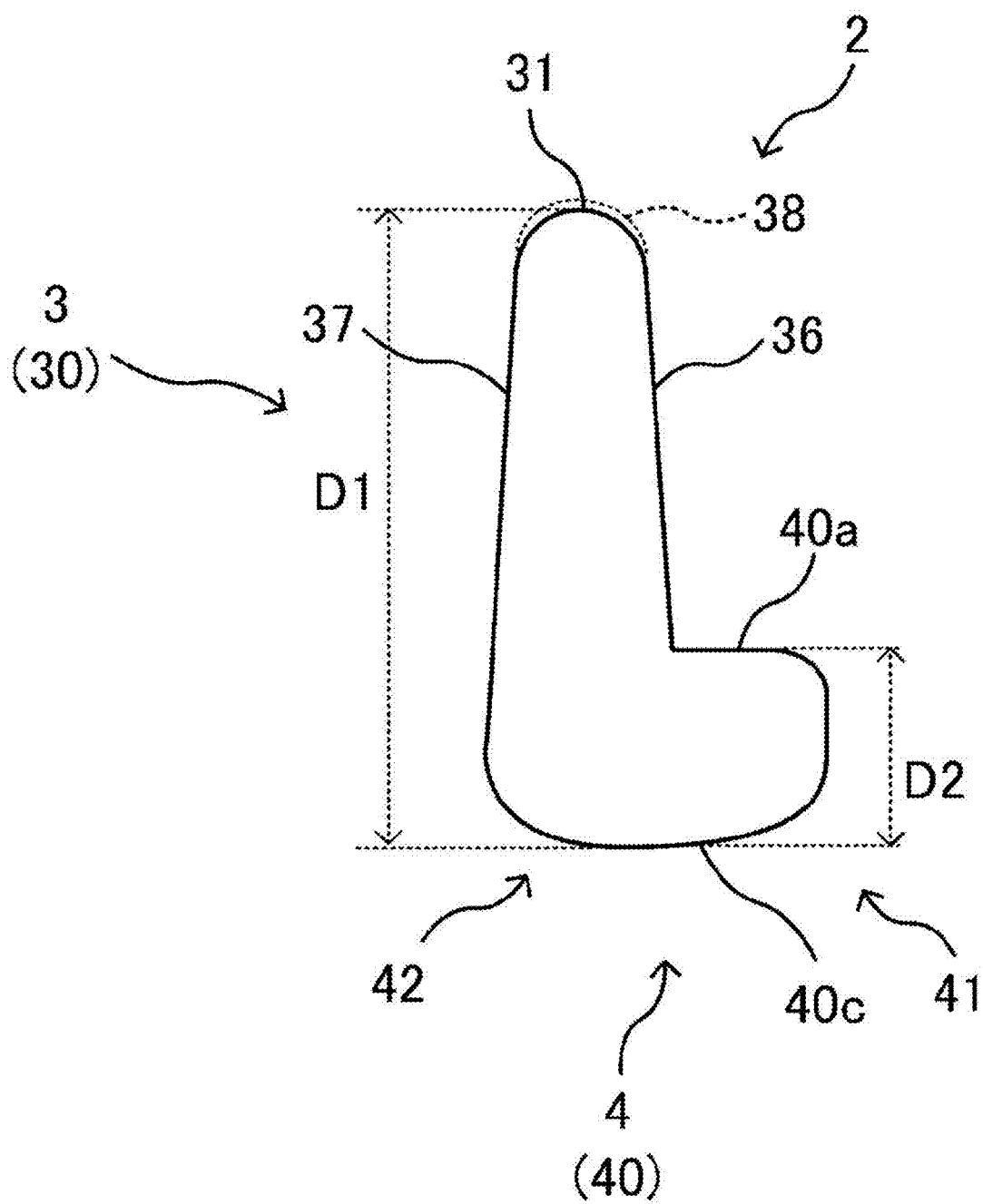
FIG. 5 is a side view showing the configuration of the pressing correction equipment of the pelvis correction equipment according to the present invention.

In using the leggings 1a made of a raw material formed of cloth fibers, the leggings 1a do not have a buffer function which a rubber raw material of the above-mentioned pelvis belt 1 has. Accordingly, as shown in FIG. 5, a pressing functional part 3 of the pressing correction equipment 2 is covered by a rubber cover 38 thus preventing the pressing functional part 3 of the equipment from directly contacting the pelvis structure. In this case, the rubber cover 38 performs a buffer function since the pressing correction equipment 2 applies a pressing contact by way of the rubber cover 38.

Further, a user may wear leggings 1a (short-pant-like mounting equipment 1a) having a surface on which a pressing position mark 10 such as a schematic view of the pelvis structure is indicated and, simultaneously, the user may tighten the leggings 1a by overlapping a strip-like transparent fastening pelvis belt on the leggings 1a ranging from a coccyx to a pelvis.

As a raw material of the pelvis fastening belt, a material having high stretchablility, high transmissivity and high fastening ability, for example, rubber, silicon, vinyl, urethane can be adopted. According to this embodiment, sizes of the pelvis fastening belt are set such that a thickness is 1.0 mm to 2.0 mm, a length is approximately 60 cm to 130 cm, and a width is approximately 150 mm to 250 cm.

It is sufficient that the pelvis fastening belt be formed of a soft material, and may have Shore hardness (Shore A) ranging from A10° to A70°, preferably ranging from A25° to A55°.

Although light transmissivity differs depending on a thickness of the pelvis fastening belt ow a wavelength (nm) of light. However, for example, in the case where the pelvis fastening belt has a thickness of 1.0 mm to 2.0 mm, a user can visually recognize the pressing position mark 10 on the surface of the leggings 1a below the pelvis fastening belt by adopting a light corresponding to a visible light having a wavelength of 300 nm to 830 nm and having light transmissivity of 60 to 100%.

In the same manner as the pelvis belt 1, an end portion of the pelvis fastening belt is fixed to a pelvis portion by wrapping in a tightened state. Accordingly, a belt overlapping fixing means such as a hook and loop fastener or engaging hooks is mounted on the pelvis fastening belt.

Due to the combination of the leggings 1a and the pelvis fastening belt, it is possible to acquire, with certainty, a pressing position indication function obtained by the leggings 1a and a pelvis fastening and fixing function and a buffer function obtained by the pelvis fastening belt.

[2. Pressing Correction Equipment]

Next, the pressing correction equipment according to this embodiment is described in detail with reference to drawings. The pressing correction equipment 2 is used for performing a pressing operation by bringing the pressing correction equipment into contact with the pressing position mark 10 on the surface of the pelvis belt 1.

The pressing correction equipment 2 is made using a hard resin or wood as a raw material. The entire surface of the pressing correction equipment 2 is roughened for preventing the pressing correction equipment 2 from slipping inadvertently on a pressing skin surface during a pressing operation as well as for allowing an operator to easily grip the pressing correction equipment 2.

Figure 4:
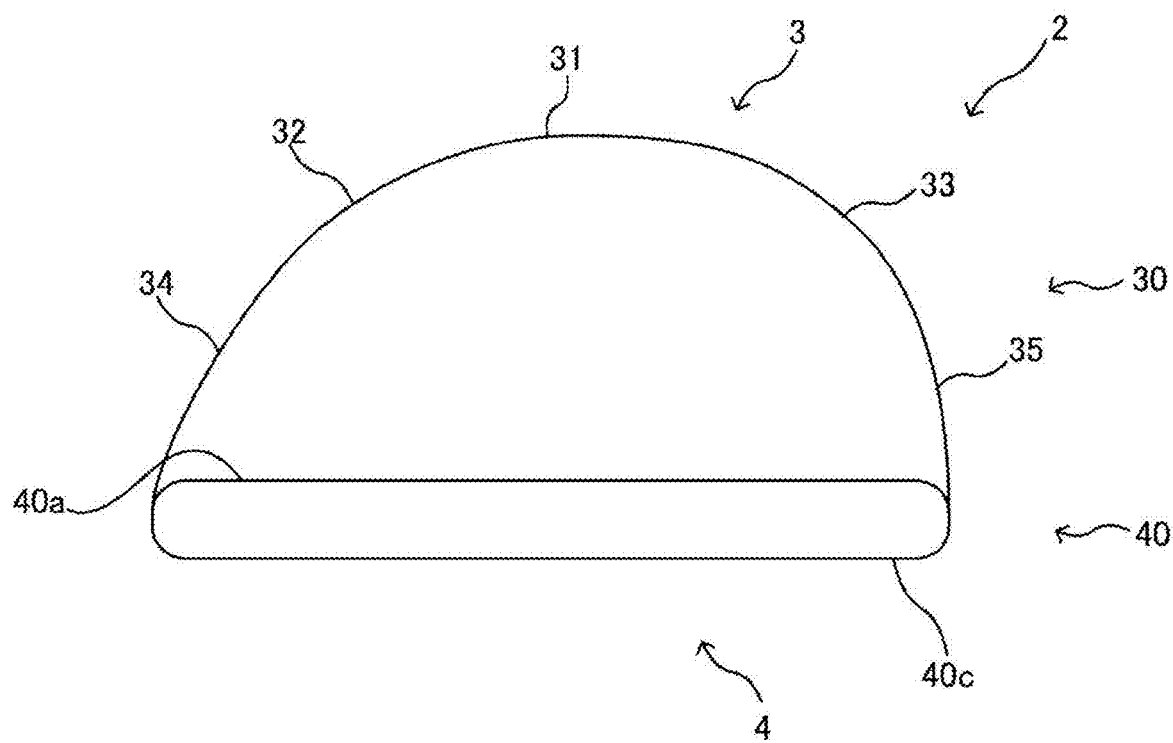
FIG. 4 is a front view showing the configuration of a pressing correction equipment of the pelvis correction equipment according to the present invention.

As shown in FIG. 4 and FIG. 5, the pressing correction equipment 2 is formed in an approximately rectangular shape as a whole as viewed in a front view and an approximately L shape in cross section. An upper end edge portion of the pressing correction equipment 2, that is, a raised side portion 30 on the pressing correction equipment 2 in an approximately L shape has an approximately straight line shape or an approximately curved shape having a gentle curve as viewed in a front view, and a thickness of the raised side portion 30 is gradually decreased toward a distal end as viewed in a side view, and the raised side portion 30 which is the upper end edge portion on the pressing correction equipment 2 forms the pressing functional part 3.

That is, the pressing correction equipment 2 is made of a hard material and is formed in an approximately L shape as viewed in a side view with a large thickness. A short side portion of the pressing correction equipment 2 having an approximately L shape forms a lateral side portion 40 which functions as the pressing grip portion 4, and a long side portion of the pressing correction equipment 2 having an approximately L shape forms a raised side portion 30 which functions as the pressing functional part 3. In this embodiment, as viewed in a side view, a wall thickness of the raised side portion 30 is set to approximately 8 to 30 mm, and a wall thickness of the lateral side portion 40 is set to approximately 5 to 40 mm.

A distal end portion of the pressing correction equipment 2 which forms the pressing functional part 3 may be made of an elastic material such as rubber or silicon. With such a configuration, when the distal end portion of the pressing functional part 3 is brought into contact with an affected part, the pressing correction equipment 2 can acquire both of a proper grip function which prevents the pressing functional part 3 From being inadvertently displaced from an affected part and a buffer function which prevents the pressing functional part 3 from applying an excessively large pressing to an affected part.

As show in FIG. 4, the raised side portion 30 includes, as viewed in a front view, a pressing upper end edge 31 positioned at a peak portion and having an approximately arcuate shape, one pressing end edge 32 extending downward from one end of the pressing upper end edge 31 and curved with a curvature lower than a curvature of the pressing upper end edge 31, the other pressing end edge 33 curved from the other end of the pressing upper end edge 31 with a curvature higher than the curvature of the pressing upper end edge 31, one side edge 34 gently curved downward from one pressing end edge 32, and the other side edge 35 inclined steeply downward from the other pressing end edge 33 and having an approximately straight line shape. The pressing upper end edge 31 formed on an upper portion of the raised side portion 30, one pressing end edge 32, and the other pressing end edge 33 are made to function as the pressing functional part in a pressing operation.

As shown in FIG. 5, an inner long side 36 and an outer long side 37 which form the raised side portion 30 of the pressing correction equipment 2 having an approximately L shape as viewed in a side view respective extend toward a distal end such that the inner long side 36 and the outer long side 37 intersect with each other thus gradually decreasing a wall thickness of the raised side portion 30. Further, the pressing upper end edge 31, one pressing end edge 32, the other pressing end edge 33 disposed on a peak portion of the raised side portion 30 which corresponds to an intersecting portion of the inner long side 36 and the outer long side 37, that is, the pressing functional part 3 is formed in a gentle curved surface.

A width of the pressing functional part 3 is set equal to or smaller than a width of each line indication of the pressing position mark 10 indicated on the pelvis belt 1 or a width of an effective correction place on a pelvis structure schematic view. In this embodiment, a wall thickness of the pressing functional part 3 is set to approximately 8 to 15 mm as viewed in a side view.

As shown in FIG. 5, the lateral side portion 40 of the pressing correction equipment 2 having an approximately L shape forms a largest wall thickness portion, and has a width D2 approximately ⅕ to ¼ of a width D1 of the raised side portion 30. The lateral side portion 40 forms the pressing grip portion 4 which is formed of: a connecting proximal end portion 42 connected to the raised side portion 30 which corresponds to a bent portion of the pressing correction equipment 2 having an approximately L shape; and a projecting stepped portion 41 projecting outward from the connecting proximal end portion 42.

The lateral side portion 40 of the pressing correction equipment 2 having an approximately L shape has: an upper surface of the projecting stepped portion 41, that is, a finger engaging stepped surface 40a which corresponds to an inner side of the pressing correction equipment 2 having an approximately L shape and has an approximately flat shape or an approximately arcuate shape; and bottom surfaces of the connecting proximal end portions 42 and the projecting stepped portion 41 which form the lateral side portion 40 of the pressing correction equipment 2 having an approximately L shape, that is, a palm contact surface 40c which corresponds to the bottom surface of the pressing correction equipment 2 having an approximately L shape and has an approximately straight-line shape or an approximately arcuate shape which corresponds to the bottom surface of the pressing correction equipment 2 having an approximately L shape.

In this embodiment, the width D1 of the raised side portion 30 is set to approximately 10 to 12 cm as viewed in a side view and the width D2 of the lateral side portion 40 of the pressing correction equipment 2 having an approximately L shape is set to approximately 2 to 2.5 cm as viewed in a side view. A length of a lateral width of the pressing grip portion 4 as viewed in a front view is set to a length which allows fingers of both hands (both fists) arranged parallel to each other to grip the pressing grip portion 4. In this embodiment, the lateral length of the pressing grip portion 4 is set to approximately 18 cm to 25 cm in this embodiment.

Figure 6:
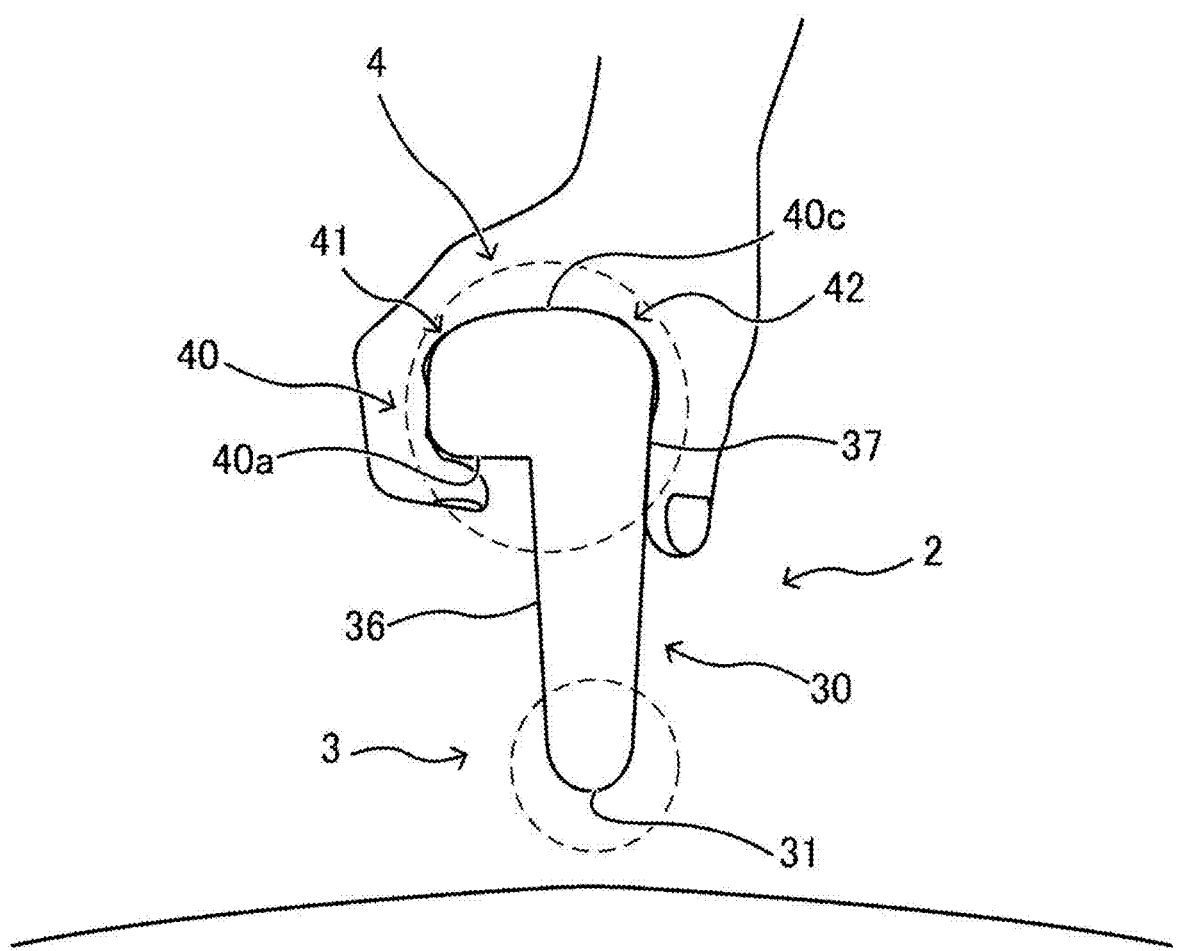
FIG. 6 is an explanatory view showing an in-use state of the pressing correction equipment of the pelvis correction equipment according to the present invention.

When an operator grips the pressing correction equipment 2, as shown in FIG. 6, the operator can firmly grip the pressing correction equipment 2 in such a manner that the operator places a thumb on a flat surface of the raised side portion 30 and other four fingers on the lateral side portion 40 of the pressing correction equipment 2 having an approximately L shape thus gripping the pressing grip portion 4 using the fingers and the palm.

Figure 7:
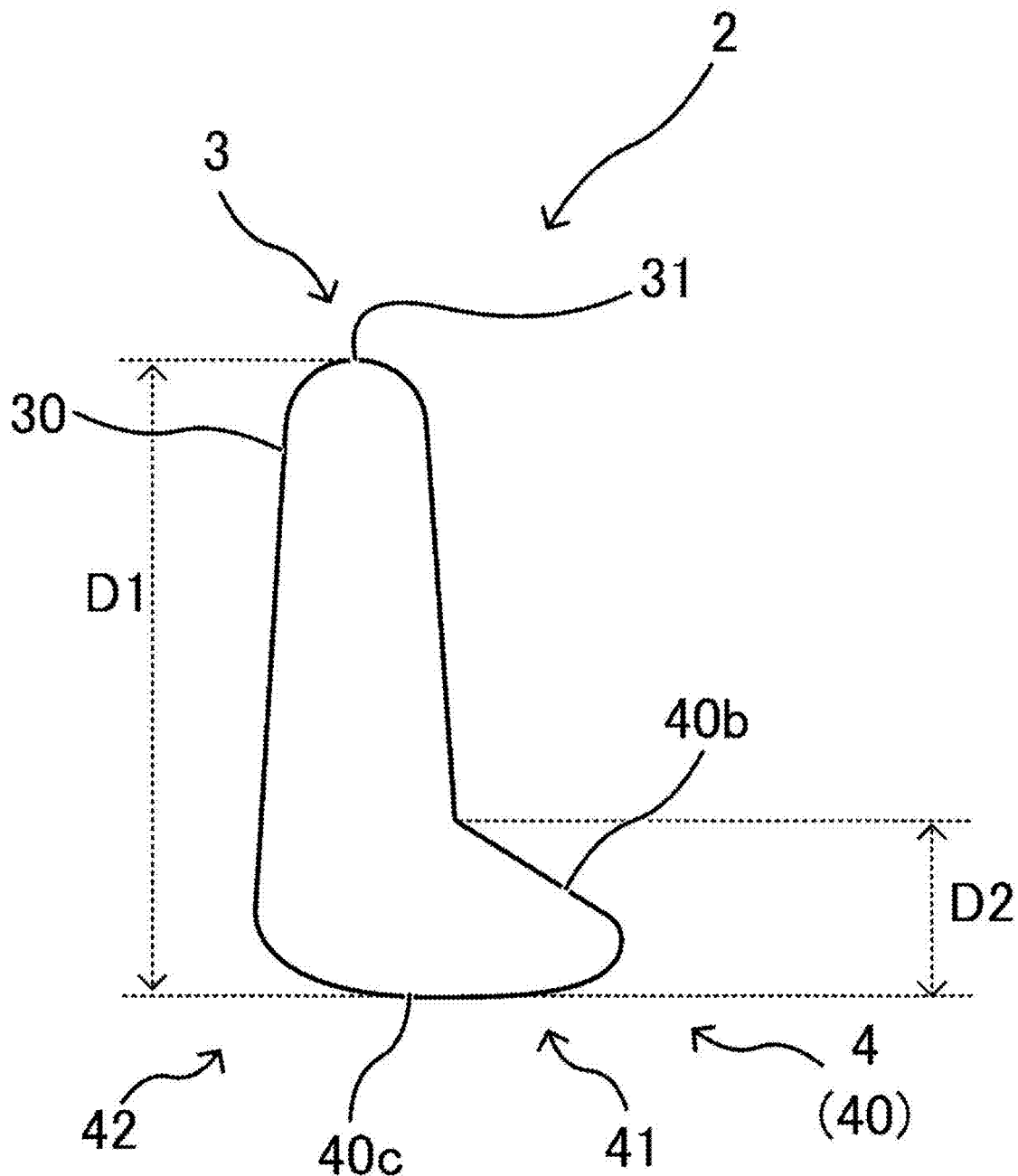
FIG. 7 is a side view showing the configuration of a modification of the pressing correction equipment of the pelvis correction equipment according to the present invention.
Figure 8:
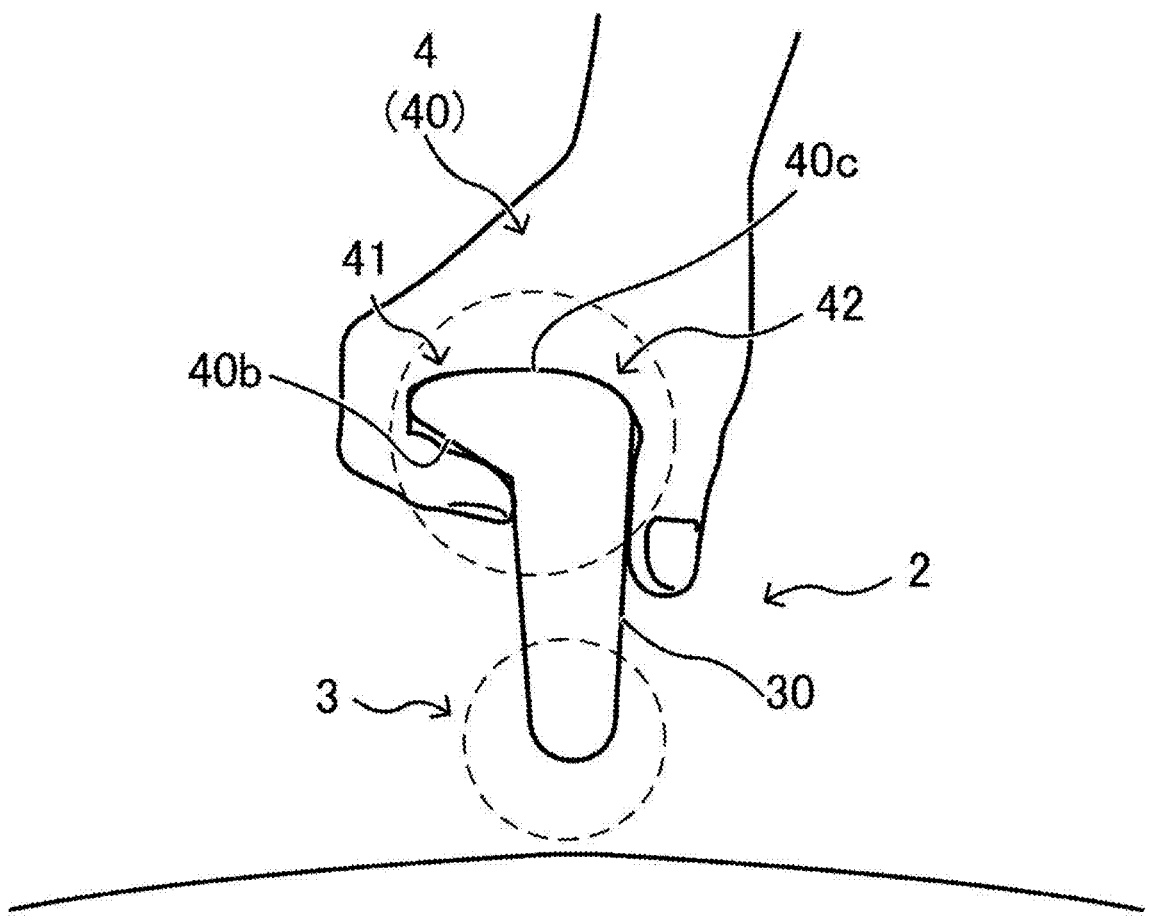
FIG. 8 is an explanatory view showing an in-use state of another modification of the pressing correction equipment of the pelvis correction equipment according to the present invention.

The finger engaging stepped surface 40a formed on the projecting stepped portion 41 of the lateral side portion 40 may be formed as an inclined grip surface 40b which is inclined downward toward a distal end of an obtuse angle bent portion on an inner side of the pressing correction equipment 2 having an approximately L shape as viewed in a side view as shown in FIG. 7.

As shown in FIG. 6 and FIG. 8 to FIG. 10, the pressing grip portion 4 is formed in a shape which enables an effective pressing operation such that the palm contact surface 40c of the lateral side portion 40 of the pressing correction equipment 2 having an approximately L shape is made to function as an end surface which becomes the center of an area to which a pressing force from an operator is applied, and a pressing force F1 generated by applying of a weight of the operator is transmitted to a distal end of the pressing functional part 3 by way of the raised side portion 30.

To be more specific, in performing a pressing operation from above the pelvis belt 1, a surface of the pressing grip portion 4 which corresponds to the connecting proximal end portion 42 of the palm contact surface 40c can be grasped such that the direction of a pressing force F1 applied from base of the palm disposed at a distal end of an arm portion of an operator becomes substantially equal to an axial direction of the raised side portion.

A surface of an operator which corresponds to the projecting stepped portion 41 of the palm contact surface 40c of the pressing grip portion 4 is formed so as to allow the operator to grip the pressing grip portion 4 such that the direction of a pressing force F2 applied at a position slightly offset from a distal end of an arm portion of the operator is directed in a direction of the pressing functional part 3 which corresponds to a peak portion of the raised side portion 30.

As a result, as shown in FIG. 10, pressing forces F1, F2 which are respectively applied to the palm contact surface 40c of the connecting proximal end portion 42 and the projecting stepped portion 41 generate a pressing force F3 which is a positive product of the pressing forces F1, F2 directed toward the pressing functional part 3.

That is, by pressing an affected part with the pressing correction equipment 2 by way of the pelvis belt 1 on which the pressing position mark 10 is indicated, it is possible to acquire an advantageous effect where a pressing force F3 concentrated on the pressing functional part 3 of the pressing correction equipment 2 can be converted into a pressing force appropriate for the affected part.

Particularly, a slip preventing function of the pelvis belt 1 and a pressing function of the pressing correction equipment 2 synergistically work so that a pressing force F3 can be grasped by the pelvis belt 1 and can be transmitted to the affected part with certainty. Accordingly correction of pelvis structure by pressing can be performed correctly and properly.

As another example, the pressing correction equipment may be formed in an approximately dew drop shape in cross section with a large thickness and in an approximately triangular shape as viewed in a front view, a portion of the pressing correction equipment having a dew drop shape ranging from a largest wall thickness portion to a distal end portion forms a raised side portion, a distal edge portion of the raised side portion is formed into a pressing functional part which has an approximately straight-line shape or a gentle approximately curved shape as viewed in a front view and gradually decreases a wall thickness toward a distal end as viewed in a side view, and a portion of the pressing correction equipment having a dew drop shape ranging from the largest wall thickness portion to a curved bottom portion may be formed as a pressing grip portion during a pressing correction operation.

Sizes of the pressing correction equipment according to this embodiment formed in an approximately dew drop shape in cross section and in an approximately triangular shape as viewed in a front view are set such that a height (a length from a curved lowermost bottom portion to a distal end portion) is set to approximately 8 to 11 cm as viewed in a side view, a thickness of a largest wall thickness portion is set to approximately 3 to 5 cm as viewed in a side view, a thickness of a distal end portion is set to approximately 0.5 to 1.5 cm as viewed in a side view, a length of the distal end portion as viewed in a front view is set to 4 to 7 cm as viewed in a front view, and
a length of the curved bottom portion is set to 18 to 20 cm as viewed in a front view.

With such a configuration, when the pressing grip portion is gripped by a human hand, a palm surface snugly fits on a curved surface from the largest wall thickness portion to the curved bottom portion at the time of gripping the pressing grip portion, and balled four fingers and the thumb fit on the curved surface of the largest wall thickness portion. Accordingly, the configuration allows an operator to naturally and securely grip the pressing grip portion so that pressing applied to a wrist of the operator during pressing therapy can be reduced.

In actually performing therapy by using the pelvis correction equipment A having a synergistic function acquired by the combination of the pelvis belt 1 and the pressing correction equipment 2, as shown in FIG. 9 to FIG. 11, an operator grips the pressing grip portion 4 of the pressing correction equipment 2 with his fingers and his palm, and performs pressing therapy by applying the pressing functional part 3 which is formed of the raised side portion 30 to the pressing position marks 10 indicated on the pelvis belt 1, that is, the above-mentioned first line L1 to the fifth line L5.

As therapy operation, an operator applies various pressing operations such as a vertical pressing operation, a lateral pressing operation and a circular pressing operation to the respective line positions of the pressing position marks 10 indicated on the pelvis belt 1 by the pressing functional part 3 of the pressing correction equipment 2.

Pressing operation modes at the respective line positions shown in FIG. 11 are described hereinafter (the directions being described hereinafter being directions of a pelvis state when a human body is in a standing posture).

With respect to the first line L1, the line indication, that is, the first line L1 is pressed in the lateral direction L1a directed toward the body axis such that the first line L1 corresponds to a position of an approximately upper half portion on an outermost side surface of an iliac bone at the lateral half portion which forms a sacroiliac joint and a position of an outer portion of a gluteus maximus muscle.

With respect to the second line L2, the second line L2 is pressed in the oblique upward lateral direction L2a (direction toward the lowermost end position of the spine) L2a which corresponds to a position which strides over respective portions consisting of an approximately center portion of a gluteus medius muscle in an approximately upper half portion of a center portion of the lateral half iliac bone which forms a sacroiliac joint and an outer portion of a piriform muscle.

With respect to the third line L3, the third line L3 is pressed in the direction which draws a concave arc in a downward oblique direction (direction directed toward a distal end of a coccyx along an outer edge of a sacral bone) such that the third line L3 corresponds to a position which strides over the respective portions consisting of a body-axis-side portion of a piriform muscle disposed close to a sacroiliac joint, an outer side portion of a pelvic floor muscle, and a body-axis-side portion of an internal obturator muscle.

With respect to the fourth line L4, the fourth line L4 is pressed in the body axis direction directed in an oblique upward direction (direction toward a lowermost end position of a spine) such that the fourth line L4 corresponds to a position of an upper portion of an approximately lateral half portion of a pelvic floor muscle at a lateral side of a lower half portion of a sacral bone which forms a sacroiliac joint.

With respect to the fifth line L5, the fifth line L5 is pressed upward in an upright direction (direction toward a lowermost end position of the spine) L5a such that the fifth line L5 corresponds to a position of an upper portion of an approximately center portion of a pelvic floor muscle at a side edge portion ranging from a peak of a sacral bone which forms a sacroiliac joint and is positioned at a lowermost portion of the sacral bone to a coccyx.

[3. Mode of Operation Using Pelvis Correction Equipment]

Hereinafter, the mode of the operation using the pelvis correction equipment A according to the present invention is described. The pelvis belt 1 and the pressing correction equipment 2 of the pelvis correction equipment A according to the present invention have the above-mentioned configurations, and it is possible to apply a therapy operation to a patient P by making use of a synergistic effect acquired by the pelvis belt 1 and the pressing correction equipment 2.

First, as shown in FIG. 1, a patient P is laid face down in a state where the pelvis belt 1 is wrapped and tightened around a lower abdomen, that is, a pelvis of a patient P. To be more specific, as shown in FIG. 10, the overlapping fixing means 11 mounted on the end portions of the pelvis belt 1 are connected to each other on an abdomen side of the patient P, and the pelvis of the patient P is fastened by the pelvis belt 1.

In fixing the pelvis belt 1, the pelvis belt 1 is fixed by making the pressing position mark 10 displayed on a surface of the pelvis belt 1 aligned with the position which corresponds to the pelvis. Accordingly, in a state where the patient P is laid face down, the pressing position mark 10 indicated on the pelvis belt 1 is positioned on a back side and becomes a mark for a correction position.

The predetermined positional alignment between the pressing position mark 10 indicated on the pelvis belt 1 and the position on the pelvis structure of the patient P is, as shown in FIG. 10, performed by making the spine of the patient P, that is, the position of the spine (indicated by a chained line in the drawing) and the center position of each line indicated as the pressing position mark 10 or the position of the spine in the schematic view of the pelvis structure overlap with each other.

Next, as shown in FIG. 9 to FIG. 11, the pressing position mark 10 indicated on the pelvis belt 1 is pressed by the pressing correction equipment 2. That is, the pressing position mark 10 ranging from the first line L1 disposed on the outermost side to the fifth like L5 is sequentially pressed by the pressing correction equipment 2.

To be more specific, as shown in FIG. 14, in the pressing therapy on the first line L1, pressing is applied from the lateral direction L1a directed toward the body axis in a state where the pressing functional part 3 is pressed to the line indication, that is, the first line L1 formed on the surface of the pelvis belt 1 such that the line indication corresponds to an approximately upper half portion of an outermost side surface of a lateral half iliac bone which forms a sacroiliac joint and the position above an outer portion of a gluteus maximus muscle.

As a result, a pressing force in the lateral direction L1a directed toward the body axis acts on the iliac bone so that the iliac bone of the sacroiliac joint portion is made to approach a sacral bone side and, at the same time, the pressing force acts on a gluteus maximus muscle and a gluteus medius muscle disposed below the gluteus maximus muscle thus activating the gluteus maximus muscle, the gluteus medius muscle and a guadrate muscle of a thigh.

Particularly, in the pressing operation on the first line L1, a pressing force is applied to the approximately whole region L10 of the first line L1. That is, a pressing operation is performed around an outer center portion of the gluteus maximus muscle which forms the center of pressing so that a pressing force acts on an outer portion of the gluteus maximus muscle with certainty thus mainly activating the gluteus maximus muscle.

As a result, the activated gluteus maximus muscle expands and shrinks between a sacral bone and a thigh bone and between the sacral bone and a coccyx bone and hence, it is possible to perform correction by making an iliac bone and a sacral bone of a sacroiliac joint portion approach each other or separate from each other by way of a hip joint.

Next, in the pressing operation on the second line L2, a pressing force is applied to the second line L2 in the oblique upward direction L2a such that second line L2 corresponds to a position which strides over respective portions consisting of an approximately center portion of a gluteus medius muscle in an approximately upper half portion of a center portion of the lateral half iliac bone which forms a sacroiliac joint and an outer portion of a piriform muscle.

As a result, a pressing force in the oblique upward direction L2a makes an iliac bone of a sacroiliac joint portion approach a sacral bone side in the oblique upward direction, various muscles which cover the iliac bone and the sacral bone and straddle over the iliac bone and the sacral bone, that is, a gluteus medius muscle, an upper gemellus muscle, a piriform muscle and an inferior gemellus muscle.

Particularly, in the pressing operation of the second line L2, a pressing operation is applied to an approximately upper half portion L20 of the second line L2 which is an area around an approximately center portion of a gluteus medius muscle which forms the center of pressing thus mainly accelerating the activation of the gluteus medius muscle.

As a result, the activated gluteus medius muscle expands and shrinks between a thigh bone and a sacral bone and hence, it is possible to perform correction by making an iliac bone and a sacral bone of a sacroiliac joint portion approach each other or separate from each other by way of a hip joint.

Next, in the pressing operation on the third line L3, a pressing force is applied to the third line L3 in the direction which draws a concave arc in a downward oblique direction L3a such that the third line L3 corresponds to a position which strides over a body-axis-side portion of a piriform muscle disposed close to a sacroiliac joint, an outer side portion of a pelvic floor muscle, and a body-axis-side portion of an internal obturator muscle.

As a result, a pressing force in the downward oblique arcuate direction L3a makes an iliac bone approach a sacroiliac joint portion along the outside of a sacral bone and, at the same time, activates a piriform muscle, a pelvic floor muscle, an inferior gemellus muscle, and an internal obturator muscle.

Particularly, in the pressing operation of the third line L3, a pressing operation is applied to an area around an upper half portion L30 of the third line L3, that is, a body axis side portion of a piriform muscle which forms a center portion of pressing thus mainly activating a piriform muscle. As a result, the activated piriform muscle expands and shrinks between a thigh bone and a sacral bone and hence, it is possible to perform correction by making an iliac bone and a sacral bone of a sacroiliac joint portion approach each other or separate from each other by way of a hip joint.

Next, in the pressing operation of the fourth line L4, a pressing operation is performed such that a pressing force is applied to the fourth line L4 in the body axis direction directed in an oblique upward direction such that the fourth line L4 corresponds to a position of an upper portion of an approximately lateral half portion of a pelvic floor muscle at a lateral side of a lower half portion of a sacral bone which forms a sacroiliac joint.

As a result, a pressing force in the oblique upper direction L4a makes a sacral bone approach an inner side of an iliac bone in a sacroiliac joint portion and, at the same time, the pressing force activates a pelvic floor muscle.

Particularly, in the pressing operation of the fourth line L4, the activation of a pelvic floor muscle is activated by pressing an area around the approximately upper half portion L40 of the fourth line L4, that is, an upper portion of an approximately lateral half portion of a pelvic floor muscle which forms a center portion of pressing. As a result, an activated pelvic floor muscle expands and shrinks between an iliac bone and a sacral bone of a sacroiliac joint and hence, it is possible to perform correction by making the iliac bone and the sacral bone portion in a sacroiliac joint approach each other or separate from each other.

Next, in the pressing operation of the fifth line L5, the fifth line L5 is pressed upward in an upright direction L5a such that the fifth line L5 corresponds to a position of an upper portion of an approximately center portion of a pelvic floor muscle at a side edge portion ranging from a peak of a sacral bone which forms a sacroiliac joint and is positioned at a lowermost portion of the sacral bone to a coccyx.

As a result, a pressing force in a directly upward direction L5a displaces the sacral bone, the iliac bone and the vertical relative position between the sacral bone and the iliac bone in a sacroiliac joint and, at the same time, further activates a pelvic floor muscle.

Particularly, in the pressing operation of the fifth line L5, a pressing force is applied to an area around an approximately upper half portion L50 of the fifth line L5, that is, an upper portion of an approximately center portion of a pelvic floor muscle which forms a center portion of pressing thus further activating the pelvic floor muscle. Accordingly, the expansion and shrinkage of the pelvic floor muscle is activated between an iliac bone and a sacral bone so that the correction can be realized by making the iliac bone and the sacral bone of the sacroiliac joint portion approach each other or separate from each other.

It is needless to say that a therapist can perform a pressing therapy using the pressing correction equipment 2 in such a manner that he arbitrarily selects respective muscles or bones displayed on a pelvis structure view instead of respective line positions as pressing position marks 10 of the pelvis belt 1 or leggings 1a.

For example, by stimulating by pressing a guadrate muscle of a thigh indicated on a pelvis structure schematic view using the pressing correction equipment 2, the activated guadrate muscle of the thigh releases tension an area from an outside of a lower portion of an iliac bone to an outside of an upper portion of a thigh bone. As a result, pelvis correction can be realized by inclining the whole pelvis in frontward and backward direction as well as in a leftward and rightward direction and, at the same time, a waist pain can be alleviated by returning a lumbar vertebrae to a proper position.

In this manner, in performing a pressing therapy on respective lines by the pelvis correction equipment A, particularly, an operator grips the pressing grip portion 4, and performs a pressing operation along a mark of the line while securely and strongly holding the lateral side portion 40 of the pressing correction equipment 2 having an approximately L shape with his five fingers.

Due to gripping of the pressing grip portion 4 having such a shape, a pressing stress reaches sacroiliac joint tissues corresponding to the respective lines from the pressing functional part 3 by way of ligaments or muscles adhering to a pelvis so that, eventually, loosening or undesired expansion of a sacroiliac joint can be corrected.

That is, a stepwise pressing stimulus generated by the combination of the pelvis belt 1 and the pressing correction equipment 2 directly acts on an iliac bone and a sacral bone which form a pelvis thus assisting the displacement of the iliac bone and the sacral bone to proper positions. At the same time, the stepwise pressing stimulus acts on a pelvis tissue group adhering to the iliac bone and the sacral bone thus promoting the activation of the pelvis tissue group. A proper positional displacement brought about by an expansion and shrinkage of the activated pelvis tissue group enables indirect pelvis correction and hence, even after therapy, a patient can acquire a sustainable therapeutic effect brought about by activated pelvis tissue group.

As has been described heretofore, according to the pelvis correction equipment of the present invention, by recognizing the pressing position marks indicated on the surface of the pelvis belt wrapped around the pelvis tightly as the effective correction places and by using the pressing correction equipment which can exhibit the correction effect at maximum corresponding to the pelvis belt, an operation load of an operator can be reduced as much as possible, and the correction of a sacroiliac joint can be properly and rapidly performed by applying an operation to proper pressing positions.

What is claimed is:
1. A pelvis correction equipment formed of a combination of a pelvis belt and a pressing correction equipment, the pelvis correction equipment comprising:
   the pelvis belt for tightening for fastening a lower abdomen of a body, the pelvis belt being used for correcting opening of or strain on a joint portion between a sacral bone and an iliac bone which forms a pelvis;
   a pressing position mark indicated on a surface of the pelvis belt for indicating a plurality of pressing correction portions; and
   the pressing correction equipment configured to be operated in such a manner that the pressing correction equipment presses the plurality of pressing correction portions along the pressing position mark on an outer surface of the pelvis belt mounted on the lower abdomen by fastening by way of the pelvis belt, and also configured to be therapeutically operated vertically, laterally or in a semicircular shape when necessary, wherein
   a vertical cross section of the pressing correction equipment is an approximately L shape, the pressing correction equipment has an approximately rectangular shape as a whole as viewed in a front view, and the approximately rectangular shape has an upper distal edge portion formed in an approximately straight line shape or a gentle approximately curved shape as viewed in the front view,
   the pressing correction equipment comprises a peaked tip end, which is a distal end of a vertical portion of the approximately L shape and the upper distal edge portion of the approximately rectangular shape, and the peaked tip end is a pressing functional part to be pressed against an affected part of a patient from an outside of the pelvis belt via the pressing position mark on the outer surface of the pelvis belt,
   the pressing correction equipment comprises a pressing grip portion at a horizontal portion of the approximately L shape and a bottom portion of the approximately rectangular shape, the pressing grip portion is formed at a largest wall thickness portion of the pressing correction equipment, and the pressing grip portion is gripped when the pressing functional part is pressed against the affected part of the patient,
   the pelvis belt is formed of an extendable and shrinkable elastic belt, and an overlapping fixing means of a belt body is mounted on an end portion of the pelvis belt,
   the pressing position mark is a combination of longitudinal lines and a schematic view of a pelvis structure of a human body which allows a visual recognition of a pressing correction position on the pelvis,
   the longitudinal lines are printed so as to trace the pressing correction position on the schematic view of the pelvis structure, and
   the schematic view of the pelvis structure is printed
      at an eccentric position by taking into account an overlapping end portion of the pelvis belt when the pelvis belt is wrapped around a waist of the patient and is fixed by the overlapping fixing means in a longitudinal direction of the pelvis belt, and
      at a position of a back surface portion which corresponds to the waist of the patient, where an actual configuration of the pelvis structure of the patient, which corresponds to an actual pelvis structure of the patient, can be visually recognized.

2. The pelvis correction equipment formed of a combination of a pelvis belt and a pressing correction equipment according to claim 1, wherein the longitudinal lines which trace the pressing correction position on the pelvis are symmetrically located at five places on each of left and right portions of the schematic view of the pelvis structure, the longitudinal lines comprise first lines, second lines, third lines, fourth lines, and fifth lines, the first lines are arranged at positions which correspond to approximately upper half portions of outermost side surfaces of left and right half iliac bones which form a sacroiliac joint, and which also correspond to positions above outer portions of a gluteus maximus muscle, the second lines are arranged at positions which correspond to positions where each of the second lines strides over an approximately center portion of a gluteus medius muscle and an outer portion of a piriform muscle at an approximately upper half portion of a center portion of each of the left and right half iliac bones which form the sacroiliac joint, the third lines are arranged at positions which correspond to positions where each of the third lines strides over a body axis side portion of the piriform muscle located close to the sacroiliac joint, an outer portion of a pelvic floor muscle, and a body axis side portion of an internal obturator muscle, the fourth lines are arranged at positions which correspond to positions above approximately left and right half portions of the pelvic floor muscle at left and right sides of lower half portions of the sacral bone which forms the sacroiliac joint, and the fifth lines are arranged at positions which correspond to positions above an approximately center portion of the pelvic floor muscle at side edge portions extending to a coccyx from sacral bone peaks positioned at lowermost portions of the sacral bones which form the sacroiliac joint.

3. The pelvis correction equipment formed of a combination of a pelvis belt and a pressing correction equipment according to claim 1, wherein a surface of a portion of the pressing position mark indicated on the surface of the pelvis belt is roughened and has a slip preventing function so as to make slipping of the pressing functional part of the pressing correction equipment difficult.

* * * * *